(12) United States Patent
Fu et al.

(10) Patent No.: US 10,829,772 B2
(45) Date of Patent: Nov. 10, 2020

(54) UNIQUE MODULAR VECTOR DESIGN

(71) Applicant: MONSANTO TECHNOLOGY LLC, St. Louis, MO (US)

(72) Inventors: Changlin Fu, St. Louis, MO (US); Jinyuan Liu, Ithaca, NY (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 341 days.

(21) Appl. No.: 14/405,754

(22) PCT Filed: Jun. 10, 2013

(86) PCT No.: PCT/US2013/044985
§ 371 (c)(1),
(2) Date: Dec. 4, 2014

(87) PCT Pub. No.: WO2013/191950
PCT Pub. Date: Dec. 27, 2013

(65) Prior Publication Data
US 2015/0152428 A1 Jun. 4, 2015

Related U.S. Application Data

(60) Provisional application No. 61/663,444, filed on Jun. 22, 2012.

(51) Int. Cl.
| | | |
|---|---|---|
| C12N 15/00 | (2006.01) | |
| C12N 15/82 | (2006.01) | |
| C12N 15/66 | (2006.01) | |

(52) U.S. Cl.
CPC .......... *C12N 15/82* (2013.01); *C12N 15/66* (2013.01); *C12N 15/8201* (2013.01); *C12N 15/8241* (2013.01)

(58) Field of Classification Search
USPC ..................................... 435/320.1; 800/8–20
See application file for complete search history.

(56) References Cited

U.S. PATENT DOCUMENTS

| | | | |
|---|---|---|---|
| 5,192,676 A | 3/1993 | Morgan | |
| 5,595,895 A | 1/1997 | Miki et al. | |
| 6,096,523 A | 8/2000 | Parrott et al. | |
| 6,303,362 B1 | 10/2001 | Stanford et al. | |
| 6,372,429 B1 | 4/2002 | Sharon | |
| 6,808,906 B2 | 10/2004 | Shen et al. | |
| 7,034,145 B2 | 4/2006 | Shen et al. | |
| 7,045,344 B2 | 5/2006 | Kay et al. | |
| 7,090,973 B1 | 8/2006 | Breton | |
| 7,250,289 B2 | 7/2007 | Zhou | |
| 7,462,758 B2 | 12/2008 | Biesgen | |
| 7,786,344 B2 | 8/2010 | Kock et al. | |
| 7,838,287 B2 | 11/2010 | Goldsmith et al. | |
| 7,943,754 B2 | 5/2011 | Bentwich et al. | |
| 8,008,459 B2 | 8/2011 | Goldsmith et al. | |
| 8,034,994 B2 | 10/2011 | Song et al. | |
| 8,124,829 B2 * | 2/2012 | Stern ................... | A01K 67/0275 800/13 |
| 8,937,214 B2 * | 1/2015 | Gilbertson ......... | C12N 15/8216 800/264 |
| 2002/0106680 A1 | 8/2002 | Shinmyo et al. | |
| 2004/0029129 A1 | 2/2004 | Wang et al. | |
| 2004/0115642 A1 | 6/2004 | Fu | |
| 2004/0185556 A1 | 9/2004 | Reed | |
| 2005/0074785 A1 | 4/2005 | Slater et al. | |
| 2005/0074883 A1 | 4/2005 | Slater et al. | |
| 2005/0130205 A1 | 6/2005 | Slater et al. | |
| 2005/0158860 A1 | 7/2005 | Goldsmith et al. | |
| 2006/0073161 A1 | 4/2006 | Breton | |
| 2007/0042404 A1 | 2/2007 | Zhao et al. | |
| 2007/0212762 A1 | 9/2007 | Slater et al. | |
| 2008/0050808 A1 * | 2/2008 | Reed ..................... | C12N 15/64 435/320.1 |
| 2008/0050819 A1 | 2/2008 | Hillebrand et al. | |
| 2008/0066199 A1 | 3/2008 | Byrum et al. | |
| 2008/0241915 A1 | 10/2008 | Reed | |
| 2008/0276334 A1 | 11/2008 | Abad et al. | |
| 2009/0226976 A1 | 9/2009 | Reed | |
| 2009/0275086 A1 | 11/2009 | Gibson et al. | |
| 2010/0035768 A1 | 2/2010 | Gibson et al. | |
| 2010/0162436 A1 | 6/2010 | Falco et al. | |
| 2010/0192262 A1 | 7/2010 | Krichevsky | |
| 2010/0192264 A1 | 7/2010 | Kock et al. | |

(Continued)

FOREIGN PATENT DOCUMENTS

| | | |
|---|---|---|
| WO | WO 200026386 | 5/2000 |
| WO | WO 200030687 | 6/2000 |

(Continued)

OTHER PUBLICATIONS

Goderis (Plant Mol. Biol., 2002, vol. 50, No. 1, p. 17-27).*
Dafny-Yelin et al., "Delivery of multiple transgenes to plant cells," *Plant Physiol* 145(4):1118-1128, 2007.
Goderis et al., "A set of modular plant transformation vectors allowing flexible insertion of up to six expression units," *Plant Mol Biol* 50(1):17-27, 2002.
International Search Report for PCT/US2013/044985, dated Dec. 2, 2013.
Atanassov et al, "A simple, flexible and efficient PCR-fusion/Gateway cloning procedure for gene fusion, site-directed mutagenesis, short sequence insertion and domain deletions and swaps," *Plant Methods* 5:14 2009.
Bellaiche et al., I-SceI Endonuclease, a New Tool for Studying DNA Double-Strand Break Repair Mechanisms in *Drosophila*, *Genetics* 152:1037-1044, Jul. 1999.

(Continued)

*Primary Examiner* — Michael C Wilson
(74) *Attorney, Agent, or Firm* — Dentons US LLP; David Lanzotti

(57) ABSTRACT

The current invention provides a modular vector system that enables the insertion of gene expression cassettes in a recursive directional stacking fashion by rare restriction sites which requires only one type of vector. The invention also provides DNA molecules, compositions, and transgenic organisms, plants, plant tissues, plant seeds, and cells comprising recombined restriction sites for rare restriction enzymes.

9 Claims, 18 Drawing Sheets

Specification includes a Sequence Listing.

(56) References Cited

U.S. PATENT DOCUMENTS

| | | |
|---|---|---|
| 2010/0317724 A1 | 12/2010 | Barzel et al. |
| 2011/0099672 A1* | 4/2011 | Gilbertson ......... C12N 15/8216 800/300.1 |
| 2011/0185456 A1 | 7/2011 | Cheikh et al. |
| 2012/0094870 A1 | 4/2012 | Goldsmith et al. |

FOREIGN PATENT DOCUMENTS

| | | |
|---|---|---|
| WO | WO 2001/051628 | 7/2001 |
| WO | WO 2002/077183 | 10/2002 |
| WO | WO 2002081711 | 10/2002 |
| WO | WO2005001133 | 1/2005 |
| WO | WO2005040336 | 5/2005 |
| WO | WO2006126040 | 11/2006 |
| WO | WO2009017821 | 2/2009 |
| WO | WO2009103027 | 8/2009 |
| WO | WO2010040531 | 4/2010 |

OTHER PUBLICATIONS

Cost et al., "Directed assembly of DNA molecules via simultaneous ligation and digestion," *BioTechniques* 42:84-89, 2007.

Edgell, "Selfish DNA: Homing Endonucleases Find a Home," *Curr Biol* 19(3):R115-117, 2009.

Fu et al., "Rapid one-step recombinational cloning," *Nucleic Acids Res* 36(9)e54, 2008.

Gibson et al., One-step assembly in yeast of 25 overlapping DNA fragments to form a complete synthetic *Mycoplasma genitalium* genome, PNAS 105(51):20404-20409, 2008.

Karimi et al., "Building Blocks for Plant Gene Assembly," *Plant Physiology* 145:1183-1191, 2007.

Katzen et al., "Simultaneous Insertion of 2, 3, or 4 DNA Fragments Into a Single Vector," *Bioscience Technology* 18-19, 2006.

Kotera et al., "A high-throughput and single-tube recombination of crude PCR products using a DNA polymerase inhibitor and type IIS restriction enzyme," *J Biotech* 137:1-7, 2008.

Lihoradova et al., "The Homingbac baculovirus cloning system: An alternative way to introduce foreign DNA into baculovirus genomes," *J Virological Methods* 140:59-65, 2007.

Lin et al., "Efficient linking and transfer of multiple genes by a multigene assembly and transformation vector system," *PNAS* 100(10):5962-5967, 2003.

Lu et al., "Comparison of Multiple Gene Assembly Methods for Metabolic Engineering," *Applied Biochemistry and Biotechnology*, 136-140:703-710, 2007.

Pachuk et al., "Chain reaction cloning: a one-step method for directional ligation of multiple DNA fragments," *Gene* 243:19-25, 2000.

Quan et al., "Circular Polymerase Extension Cloning of Complex Gene Libraries and Pathways," *PLoS ONE* 4(7): e6441, 2009.

Rouchka et al., "Sequence Assembly Validation by Multiple Restriction Digest Fragment Coverage Analysis," from the Proceedings of the Sixth International Conference on Intelligent Systems for Molecular Biology (ISMB-98), American Association for Artificial Intelligence, 1998.

Tsuge et al., "One step assembly of multiple DNA fragments with a designed order and orientation in *Bacillus subtilis* plasmid," *Nucleic Acids Research* 31(21):e133, 2003.

Wentzell et al., "The SfiI Restriction Endonuclease Makes a Four-strand DNA Break at Two Copies of its Recognition Sequence," *J Mol Biol* 248:581-595, 1995.

Zuo et al., "One-step DNA Fragment Assembly and Circularization for Gene Cloning," *Curr Issues Mol Biol* 12:11-16, 2010.

Sleight, "BBF RFC 26: In-Fusion BioBrick Assembly," available at <http://dspace.mit.edu/bitstream/handle/1721.1/46328/bbf%20rfc%2026_070709.pdf?sequence=1>, accessed Jun. 29, 2015.

I-ScseI product sheet, Catalog No. ER1771, Fermentas Life Sciences, available at <http://search.cosmobio.co.jp/cosmo_search_p/search_gate2/docs/FER_/ER1771.20060615.pdf>, accessed Jun. 29, 2015.

Knight, "Indempotent Vector Design for Standard Assembly of Biobricks," available at <http://web.mit.edu/synbio/release/docs/biobricks.pdf>, accessed Jun. 29, 2015.

Invitrogen Gateway product sheet, 2008.

Safety Data Sheet for I-Scel-I, New England Biolabs, available at <https://www.neb.com/~/media/Catalog/All-Products/1241BC4F73CF4AA0BEADB7CFB6C35058/MSDS/sdsR0694gh.pdf>, accessed Jun. 29, 2015.

* cited by examiner

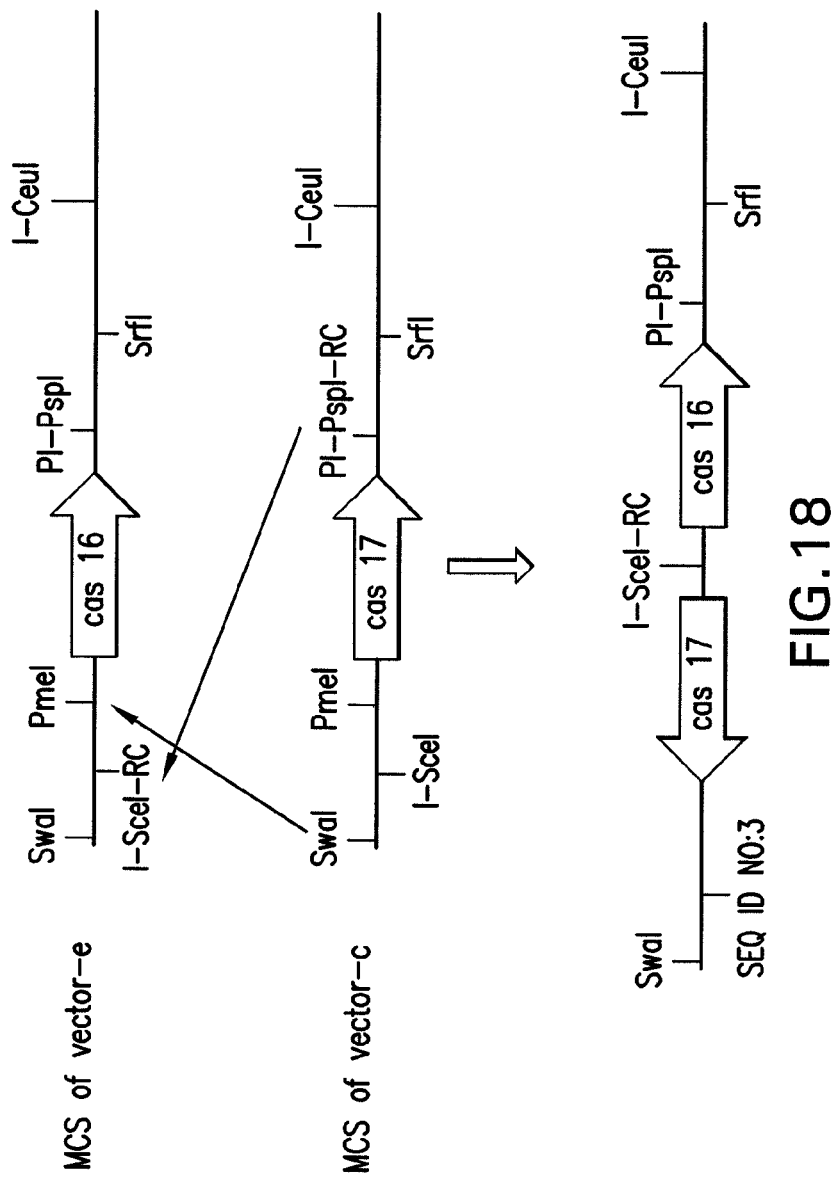

SEQUENCE LISTING

```
<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Nucleotide sequence of the recombined sites for
      I-SceI and the reverse complemented PI-PspI (PI-PspI-RC)
      restriction site after digestion with I-SceI and PI-PspI
```

```
<400> SEQUENCE: 1
tagggataat agctgtttgc ca                                              22

<210> SEQ ID NO 2
<211> LENGTH: 26
<212> TYPE: DNA
<213> ORGANISM: Artificial Sequence
<220> FEATURE:
<223> OTHER INFORMATION: Nucleotide sequence of the recombined sites for
      the reverse complemented PI-PspI (PI-PspI-RC) and restriction site
      for I-SceI after digestion with I-SceI and PI-PspI

<400> SEQUENCE: 2
acccataata cccataacag ggtaat                                          26

<210> SEQ ID NO 3
<211> LENGTH: 26
<212> TYPE: DNA
<213> ORGANISM: Artificial Sequence
<220> FEATURE:
<223> OTHER INFORMATION: Nucleotide sequence of the recombined sites for
      the reverse complemented I-SceI (I-SceI-RC) and PI-PspI
      restriction sites after digestion with I-SceI and PI-PspI

<400> SEQUENCE: 3
attaccctgt tatgggtatt atgggt                                          26

<210> SEQ ID NO 4
<211> LENGTH: 22
<212> TYPE: DNA
<213> ORGANISM: Artificial Sequence
<220> FEATURE:
<223> OTHER INFORMATION: Nucleotide sequence of the recombined sites for
      PI-PspI and the reverse complemented I-SceI (I-SceI-RC)
      restriction sites after digestion with I-SceI and PI-PspI

<400> SEQUENCE: 4
tggcaaacag ctattatccc ta                                              22

<210> SEQ ID NO 5
<211> LENGTH: 18
<212> TYPE: DNA
<213> ORGANISM: Artificial Sequence
<220> FEATURE:
<223> OTHER INFORMATION: Restriction site of the homing enzyme I-SceI

<400> SEQUENCE: 5
tagggataac agggtaat                                                   18

<210> SEQ ID NO 6
<211> LENGTH: 30
<212> TYPE: DNA
<213> ORGANISM: Artificial Sequence
<220> FEATURE:
<223> OTHER INFORMATION: Restriction site of the homing enzyme PI-PspI

<400> SEQUENCE: 6
tggcaaacag ctattatggg tattatgggt                                      30

<210> SEQ ID NO 7
<211> LENGTH: 26
<212> TYPE: DNA
<213> ORGANISM: Artificial Sequence
<220> FEATURE:
<223> OTHER INFORMATION: Restriction site of the homing enzyme I-CeuI

<400> SEQUENCE: 7
```

```
taactataac ggtcctaagg tagcga                                          26

<210> SEQ ID NO 8
<211> LENGTH: 30
<212> TYPE: DNA
<213> ORGANISM: Artificial Sequence
<220> FEATURE:
<223> OTHER INFORMATION: Reverse complement of the restriction site of
      the homing enzyme PI-PspI (PI-PspI-RC)

<400> SEQUENCE: 8
acccataata cccataatag ctgtttgcca                                      30

<210> SEQ ID NO 9
<211> LENGTH: 18
<212> TYPE: DNA
<213> ORGANISM: Artificial Sequence
<220> FEATURE:
<223> OTHER INFORMATION: reverse complement of the restriction site of
      the homing enzyme I-SceI (I-SceI-RC)

<400> SEQUENCE: 9
attaccctgt tatccta                                                    18

<210> SEQ ID NO 10
<211> LENGTH: 27
<212> TYPE: DNA
<213> ORGANISM: Artificial sequence
<220> FEATURE:
<223> OTHER INFORMATION: 5' promoter adaptor containing AscI site

<400> SEQUENCE: 10
ctgcttggcc tactaggccg gcgcgcc                                         27

<210> SEQ ID NO 11
<211> LENGTH: 28
<212> TYPE: DNA
<213> ORGANISM: Artificial sequence
<220> FEATURE:
<223> OTHER INFORMATION: 3' promoter adaptor containing SfiI2 site

<400> SEQUENCE: 11
ggtacctggc cagtctggcc tcggtccg                                        28

<210> SEQ ID NO 12
<211> LENGTH: 28
<212> TYPE: DNA
<213> ORGANISM: Artificial sequence
<220> FEATURE:
<223> OTHER INFORMATION: 5' GOI adaptor containing SfiI2 site

<400> SEQUENCE: 12
cggaccgagg ccagactggc caggtacc                                        28

<210> SEQ ID NO 13
<211> LENGTH: 28
<212> TYPE: DNA
<213> ORGANISM: Artificial sequence
<220> FEATURE:
<223> OTHER INFORMATION: 3' GOI adaptor containing SfiI3 site

<400> SEQUENCE: 13
gggccctggc cacagtggcc ttaattaa                                        28

<210> SEQ ID NO 14
```

```
<211> LENGTH: 28
<212> TYPE: DNA
<213> ORGANISM: Artificial sequence
<220> FEATURE:
<223> OTHER INFORMATION: 5' 3'UTR adaptor containing SfiI3 site

<400> SEQUENCE: 14
ttaattaagg ccactgtggc cagggccc                                              28

<210> SEQ ID NO 15
<211> LENGTH: 28
<212> TYPE: DNA
<213> ORGANISM: Artificial sequence
<220> FEATURE:
<223> OTHER INFORMATION: 3' 3'UTR adaptor containing SfiI4 site

<400> SEQUENCE: 15
gctcgtggcc gtcacggcca cctgcagg                                              28

<210> SEQ ID NO 16
<211> LENGTH: 13
<212> TYPE: DNA
<213> ORGANISM: Artificial sequence
<220> FEATURE:
<223> OTHER INFORMATION: Restriction site for SfiI enzyme
<220> FEATURE:
<221> NAME/KEY: misc_feature
<222> LOCATION: (5)..(9)
<223> OTHER INFORMATION: n is a, c, g, or t

<400> SEQUENCE: 16
ggccnnnnng gcc                                                              13
```

UNIQUE MODULAR VECTOR DESIGN

REFERENCE TO RELATED APPLICATIONS

This application is a 371 National Stage Entry of PCT/US2013/44985, filed Jun. 10, 2013, which claims the priority of U.S. Provisional Application Ser. No. 61/663,444, filed Jun. 22, 2012, the entire disclosure of which are specifically incorporated herein by reference.

FIELD OF THE INVENTION

The invention relates generally to the fields of molecular biology, genetics, and plant breeding. More particularly, the invention relates to the construction and composition of unique vectors for transformation of plants.

INCORPORATION OF SEQUENCE LISTING

The sequence listing contained in the file named "MONS310USrevised_ST25.txt", which is 4.33 kilobytes (size as measured in Microsoft Windows®) and was created on Dec. 8, 2017, is filed herewith by electronic submission and is incorporated by reference herein.

BACKGROUND OF THE INVENTION

To achieve desired traits or phenotypes in a plant, the introduction of more than one transgene is often needed. Rather than performing multiple transformation steps with multiple vectors, a single vector containing multiple individual transgenes in gene expression cassettes may be used. It is often necessary to test these multiple gene expression cassettes in different orders and orientations to each other to find the arrangement that elicits the most advantageous phenotype.

BRIEF SUMMARY OF THE INVENTION

The present invention provides novel recombinant DNA molecules comprising SEQ ID NO: 1, 2, 3, or 4, which are useful to assemble gene expression cassettes, and methods of assembling gene expression cassettes. Other embodiments of the invention provide novel recombinant DNA molecules useful to stack multiple gene expression cassettes and methods to stack multiple gene expression cassettes in a vector. In an embodiment, the novel recombinant DNA molecules comprise vectors. One embodiment of the present invention provides recombinant DNA molecules comprising arrangements of rare restriction enzyme recognition sites compatible with each other. Additional embodiments of the invention provide transgenic organisms, transgenic plants or plant tissues, transgenic plant seeds, and transgenic cells that comprise SEQ ID NO:1, 2, 3, or 4 or comprise at least two gene expression cassettes introduced by vectors of this invention. Another embodiment of the present invention provides transgenic organisms, transgenic plants or plant tissues, transgenic plant seeds and transgenic cells that comprise SEQ ID NO:1, 2, 3, or 4 between at least two DNA molecules or gene expression cassettes. Further embodiments of the invention provide the recombined sequences of I-SceI and PI-PspI-RC (SEQ ID NO:1 or 2) and the recombined sequences of I-SceI-RC and PI-PspI (SEQ ID NO:3 or 4. SEQ ID NO:1, 2, 3, or 4 may be used to identify vector stacks, transgenic organisms, transgenic plants or plant tissues, transgenic plant seeds, and transgenic cells that harbor recombinant DNA molecules with rare restriction sites as outlined herein that were stacked by methods of the present invention. In other embodiments of this invention, the stacked recombinant DNA molecules comprise gene expression cassettes that were stacked by methods of the present invention in vectors of this invention.

In one aspect, the invention provides the recombined sequences of the I-SceI and PI-PspI-RC and I-SceI-RC and PI-PspI restriction sites (SEQ ID NO:1, 2, 3, or 4).

In another aspect, the present invention provides a transgenic organism, a transgenic plant or plant tissue, a transgenic plant seed, a transgenic cell or a vector that comprises SEQ ID NO:1, 2, 3, or 4.

In a further aspect, the present invention provides a transgenic organism, transgenic plant or plant tissue, transgenic plant seed and transgenic cell that comprise SEQ ID NO:1, 2, 3, or 4 between at least two gene expression cassettes, or adjacent to a gene expression cassette.

In yet a further aspect, the invention provides a vector comprising a first grouping or arrangement of rare restriction enzyme recognition sites, having a first recognition site for a first rare restriction enzyme producing an overhang, a second recognition site for a second rare restriction enzyme producing a blunt end, and a third recognition site for a third rare restriction enzyme producing an overhang; and a second arrangement of rare restriction enzyme recognition sites having a fourth recognition site for a fourth rare restriction enzyme producing a blunt end, a fifth recognition site for a fifth rare restriction enzyme producing an overhang, and a sixth recognition site for a sixth rare restriction enzyme producing a blunt end, wherein joining of the overhang produced by the first or second rare restriction enzyme with the overhang produced by the fifth restriction enzyme eliminates the first or third and the fifth recognition site.

In an additional aspect of the present invention the first, third, and fifth rare restriction enzymes are homing enzymes.

In another aspect of the present invention the compatible ends, provided by cleavage of the reverse compliment recognition sequences of homing enzymes PI-PspI and I-SceI with the respective homing enzyme, that upon irreversibly recombining with complimentary ends, eliminate two of the first, third, or fifth recognition sites.

In yet another aspect of the present invention the recombination of the overhang produced by said first or second rare restriction enzyme with the overhang produced by said fifth restriction enzyme generates SEQ ID NO:1, 2, 3, or 4.

In still another aspect, the construct provided by the invention further comprises a gene expression cassette flanked by the first and the second arrangement of rare restriction enzyme recognition sites.

In a further aspect the present invention provides a gene expression cassette that is flanked by the first and second arrangement of rare restriction enzyme recognition sites of the vector.

In a further aspect the present invention provides a vector that comprises a recognition site for I-CeuI; a recognition site for SrfI; a recognition site for PI-PspI, wherein the recognition site for PI-PspI is in reverse complemented orientation; a recognition site for PmeI; a recognition site for I-SceI; and a recognition site for SwaI.

In a further aspect, this invention provides a vector that comprises a recognition site for I-CeuI, a recognition site for SrfI, a recognition site for I-SceI, wherein the recognition site for I-SceI is in reverse complemented orientation, a recognition site for PmeI, a recognition site for PI-PspI, and a recognition site for SwaI. I-CeuI, SrfI, PI-PspI, I-SceI, PmeI and SwaI are names for specific restriction endonucleases.

In another aspect, the present invention provides a method for stacking at least two gene expression cassettes, comprising obtaining a first plasmid vector; cutting the first vector with two rare restriction enzymes to linearize the vector; obtaining a second vector; cutting the second vector with two rare restriction enzymes and isolating a gene expression cassette of the second vector; and combining the linearized vector and the isolated gene expression cassette to assemble a vector comprising at least two gene expression cassettes.

Furthermore, another aspect of the present invention provides a method for stacking at least two gene expression cassettes, wherein the first vector or the second vector comprises at least two gene expression cassettes.

Another aspect of this invention provides a method of stacking at least two gene expression cassettes into a vector comprising linearizing a first vector comprising one or more gene expression cassette(s) with a first set of two rare restriction enzymes; isolating a second gene expression cassette from a second plasmid vector with a second set of two rare restriction enzymes; introducing the second gene expression cassette into the linearized first plasmid vector; whereby a first recognition site of the first set or the second set of two rare restriction enzymes is retained, a second recognition site of the first set or the second set of two rare restriction enzymes is lost, and whereby the second gene expression cassette reintroduces the recognition site that was lost.

BRIEF DESCRIPTION OF THE FIGURES

FIG. 18: Shows generation of SEQ ID NO:3 upon recombination using a vector having MCS of vector-e configuration and another vector in MCS of vector-c configuration.

BRIEF DESCRIPTION OF THE SEQUENCES

Figure 1:
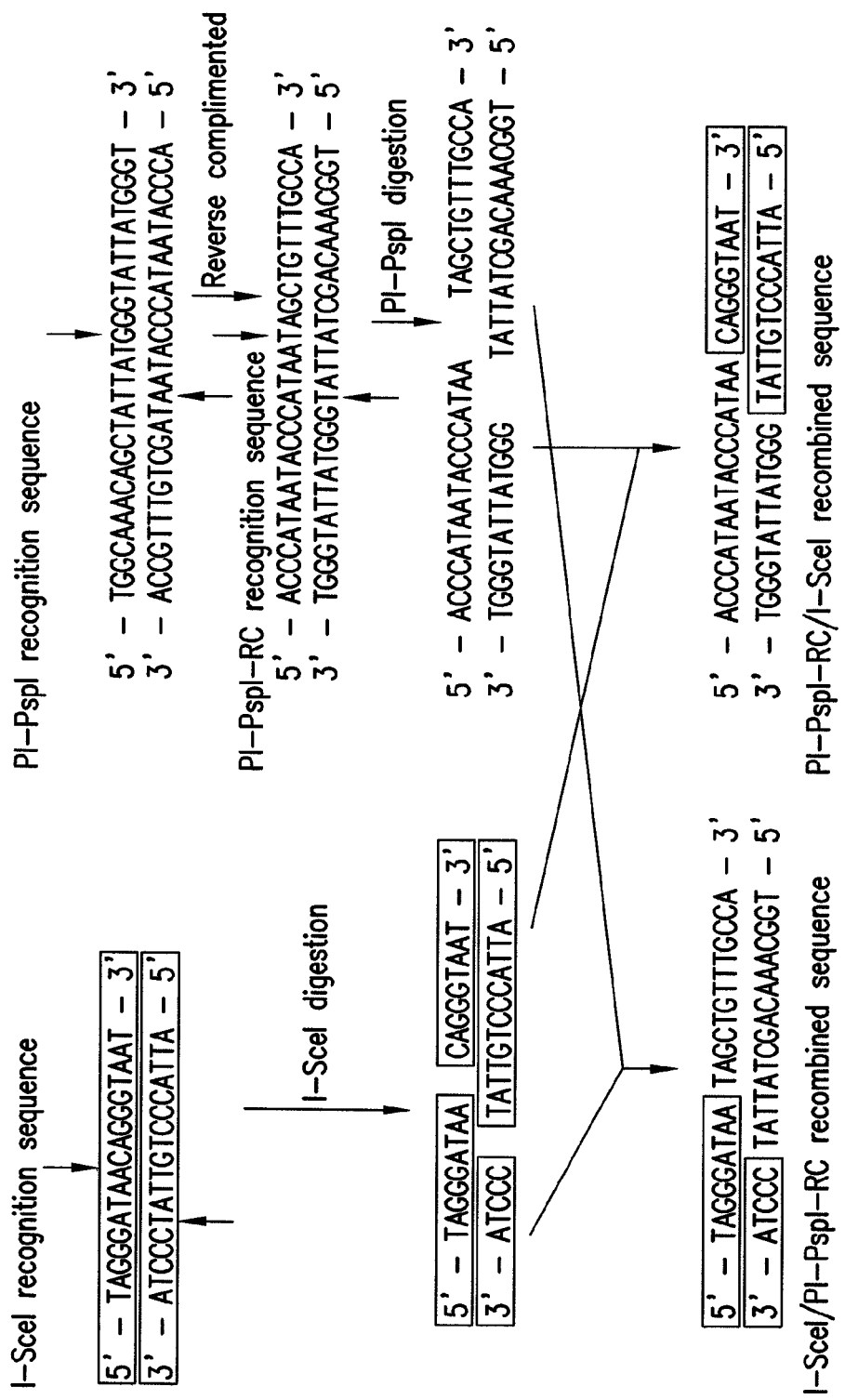
FIG. 1: Shows that by reverse complementing the orientation of the PI-PspI recognition site (called PI-PspI-RC) in the vector, the resulting overhang upon digestion is compatible with the overhang produced by I-SceI. I-SceI recognition sequence (SEQ ID NO:5) and reverse complement thereof (before and after digestion), PI-PspI recognition sequence (SEQ ID NO:6) and reverse complement thereof, PI-PspI-RC recognition sequence (SEQ ID NO:8) and reverse complement thereof (before and after digestion) are shown. Upon recombination of the I-SceI- and PI-PspI-generated overhangs, one of SEQ ID NO:1-2 is produced.
Figure 2:
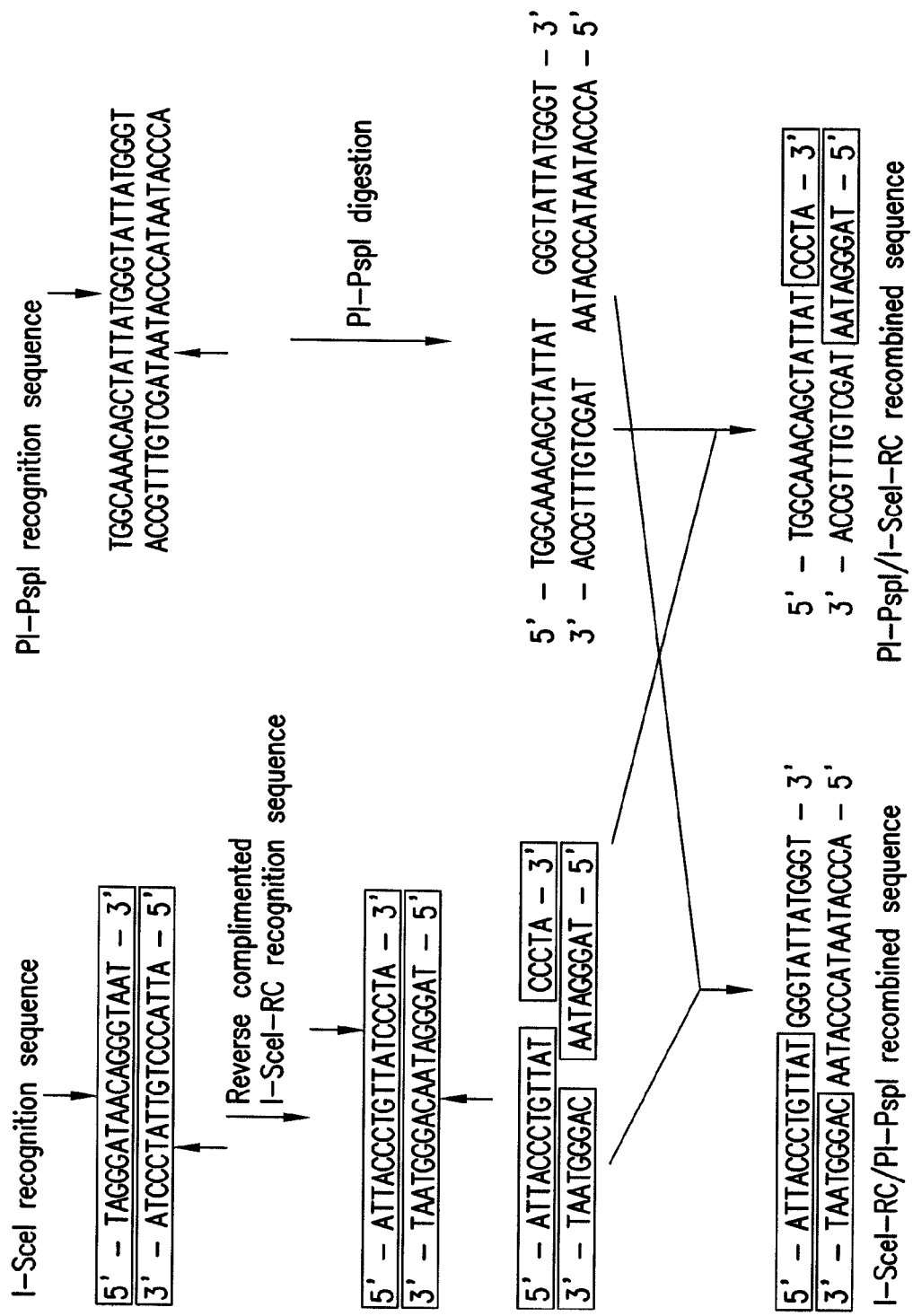
FIG. 2: Shows that the I-SceI site can also be used in the reverse complement orientation (called I-SceI-RC) to produce overhangs that are compatible with overhangs generated by PI-PspI. I SceI recognition sequence (SEQ ID NO:5) and reverse complement thereof, ISceI-RC recognition sequence (SEQ ID NO:9) and reverse complement thereof (before and after digestion), PI-PspI recognition sequence (SEQ ID NO:6) and reverse complement thereof (before and after digestion) are shown. The recombined sequences of the I-SceI and PI-PspI generated overhangs are SEQ ID NO:3-4.

SEQ ID NO:1—Nucleotide sequence of the recombined sites for I-SceI and the reverse complemented PI-PspI (PI-PspI-RC) restriction site after digestion with I-SceI and PI-PspI.

SEQ ID NO:2—Nucleotide sequence of the recombined sites for the reverse complemented PI-PspI (PI-PspI-RC) and restriction site for I-SceI after digestion with I-SceI and PI-PspI.

SEQ ID NO:3—Nucleotide sequence of the recombined sites for the reverse complemented I-SceI (I-SceI-RC) and PI-PspI restriction sites after digestion with I-SceI and PI-PspI.

SEQ ID NO:4—Nucleotide sequence of the recombined sites for PI-PspI and the reverse complemented I-SceI (I-SceI-RC) restriction sites after digestion with I-SceI and PI-PspI.

SEQ ID NO:5—Restriction site of the homing enzyme I-SceI.

SEQ ID NO:6—Restriction site of the homing enzyme PI-PspI.

SEQ ID NO:7—Restriction site of the homing enzyme I-CeuI.

SEQ ID NO:8—Reverse complement of the restriction site of the homing enzyme PI-PspI (PI-PspI-RC).

SEQ ID NO:9—Reverse complement of the restriction site of the homing enzyme I-SceI (I-SceI-RC).

ILLUSTRATIVE EMBODIMENTS OF THE INVENTION

The present invention provides novel vectors that function both as shuttle vectors and docking vectors. The vectors of the invention enable the assembly of multiple gene expression cassettes in various orders and orientations to each other without the need to design special flanking sequences for each of the gene expression cassettes in the various possible vector stacks. The present invention also provides methods to assemble vector stacks in a recurrent fashion in any direction and/or order. Moreover, the invention provides the reverse compliment recognition sequence of the homing enzyme PI-PspI (PI-PspI-RC) that, upon cleavage with PI-PspI, provides complimentary ends to the ones generated by the homing enzyme I-SceI, thereby combining the benefits of a large restriction enzyme recognition site with the directed and irreversible recombination (or combination) of the PI-PspI-RC and I-SceI sites. Further this invention provides the reverse compliment recognition sequence of the homing enzyme I-SceI (I-SceI-RC). Upon digestion with I-SceI the generated overhangs are compatible with the overhangs produced by PI-PspI.

The present invention provides an advantage over currently available technology. Several cloning methods are available to either assemble the gene expression cassette or stack individual gene expression cassettes in one single vector. However, these methods are limited in that more than one type of plasmid vector is needed, e.g., a shuttle vector to assemble the individual gene expression cassettes with predetermined flanking sequences, and docking vectors that receive the gene expression cassettes from the shuttle vector in the order and orientation that is determined by those individual flanking sequences of the individual gene expression cassettes (U.S. Pat. No. 6,096,523; U.S. Patent Pub. No. 2008/0241915). These methods are also limited in that the order and direction of the individual elements in the gene expression cassette or the order and direction of multiple gene expression cassettes in a single vector has to be determined in advance to build the plasmid vector. A plasmid vector and a method for cloning is needed in the art that does not require previous knowledge of the sequence and direction of multiple gene expression cassettes in one plasmid vector and does not necessitate the use of docking and shuttle vectors, but rather only one type of vector.

As used herein, "a" or "an" may mean one or more. As used herein in the claim(s), when used in conjunction with the word "comprising," the words "a" or "an" may mean one or more than one.

As used herein the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, "arrangement" refers to a group of restriction enzyme recognition sites found in a vector. This group may consist of homing enzymes as well as rare restriction enzymes producing 3' or 5' overhangs or blunt ends. If this arrangement of restriction sites is neighboring a gene expression cassette, it is said that the arrangement is flanking the gene expression cassette.

As used herein, "cognate sequence" refers to the minimal string of nucleotides that are required for a restriction enzyme to bind and cleave a DNA molecule or gene.

As used herein, "compatible and cohesive ends" are produced when two separate restriction enzymes have similar but non-identical recognition sites and cut the DNA producing overhangs that can hydrogen-bond or anneal with each other. After annealing and ligation, the resulting recombined site cannot be cut by either of the two restriction enzymes. Any restriction enzyme that produces either a 3' or 5' overhang upon cleavage results in a DNA fragment with sticky or cohesive ends that can recombine with an overhang of a complementary sequence. The annealing of two compatible ends, as well as of two compatible and cohesive ends, is called recombination. As used herein, "construct" refers to an engineered polynucleotide molecule, e.g., a plasmid or vector.

As used herein, "DNA fragment" refers to any molecule of DNA, including but not limited to a protein-coding sequence, reporter gene, promoter, enhancer, intron, exon, poly-A tail, multiple cloning site, nuclear localization signal, or mRNA stabilization signal, or any other naturally occurring or synthetic DNA molecule. Alternatively, a DNA fragment may be completely of synthetic origin, produced in vitro. Furthermore, a DNA fragment may comprise any combination of isolated naturally occurring and/or synthetic fragments.

As used herein, "element" refers to a region of nucleic acid sequence that imparts a particular function or structural characteristic upon the molecule.

As used herein, "expression" refers to the combination of intracellular processes, including transcription. In the case of a functional RNA sequence, such as an antisense RNA, siRNA, or microRNA, expression may involve transcription and processing of the functional RNA. In the case of a polypeptide, coding sequence expression includes transcription and translation to produce a polypeptide.

As used herein, "flanking" refers to sites upstream and downstream of one or more elements, e.g., one or more gene expression cassettes. If a gene expression cassette is in reverse orientation, e.g. cassette 6 in the triple stack vector of FIG. 10, upstream refers to the left side of the cassette, and downstream refers to the right side of the cassette.

As used herein, "fragment" refers to an individual nucleic acid molecule that can be hybridized or connected with one or more other fragment molecules to produce a hybrid molecule.

As used herein, "gene expression cassette" refers to one or more transgene operably linked to nucleic acid sequences that control expression of the transgene in a cell. The term gene expression cassette, expression cassette, and cassette are used interchangeably.

As used herein, "gene expression element" refers to expression control sequences that include but are not limited to promoters, enhancers, insulators, introns, terminators, and internal ribosome entry sites. Gene expression elements are combined with one or more genes of interest, or transgenes, into a gene expression cassette and govern the expression of the one or more transgenes in a desired way.

As used herein, "genetic transformation" refers to a process of introducing a DNA sequence or construct (e.g., a vector or gene expression cassette) into a cell or protoplast in which a heterologous DNA is incorporated into a chromosome or is capable of autonomous replication.

As used herein, "gene-of-interest (GOI)" refers to the transgene conferring the desired phenotype, e.g., herbicide or insect resistance. The GOI is part of the gene expression cassette.

As used herein "heterologous" refers to a sequence which is not normally present in a given host genome in the genetic context in which the sequence is currently found. In this respect, the sequence may be native to the host genome, but rearranged with respect to other genetic sequences within the host sequence. For example, a regulatory sequence may be heterologous in that it is linked to a different coding sequence relative to the native regulatory sequence. Furthermore, sequences and DNA molecules of the present invention may be heterologous to the organism, plant or cell they are comprised in.

As used herein, "homing enzyme" refers to an endonuclease having a double-stranded DNA recognition site of greater than 14 base pairs (bp). Homing enzymes also belong to the class of rare restriction enzymes, although not all rare restriction enzymes are homing enzymes. A homing enzyme is also called "HE," or in some cases "meganuclease." Examples of homing enzymes are I-SceI, I-CeuI, PI-PspI, and I-PpoI. Homing enzymes may occur naturally, may be engineered, or they may be synthetic.

As used herein, "isolating" refers to any process that allows the release of a DNA fragment from a larger DNA fragment. For example, a gene expression cassette can be isolated from a larger DNA fragment, e.g., a vector, by cutting the vector with restriction enzymes that flank the gene expression cassette. Often, the isolated DNA fragment is subsequently purified.

As used herein, "connect" and "connection" refer to any reaction that results in formation of a covalent bond between two nucleic acid molecules that were not covalently attached to one another prior to the reaction and which does not require introduction of an exogenous ligase enzyme. In an embodiment, two gene expression cassettes can be connected in a vector to form a double-vector stack. In other embodiments, double-vector stacks can be combined with another gene expression cassette to form a triple-vector stack. Still other embodiments may combine gene expression cassettes together to form vector stacks with 4, 5, 6, 7, 8, 9, or 10 or more gene expression cassettes.

As used herein, "modular" refers to elements in a DNA construct that can be readily removed from the construct. For example, modular elements in a construct have unique pairs of restriction sites flanking each element within the construct, enabling the exclusive manipulation of individual elements.

As used herein, "multiple cloning site" or "MCS" refers to a short region of DNA which contains multiple restriction sites to allow insertion of DNA fragments at this location.

As used herein, "obtaining" refers to either isolating or generating a desired component.

As used herein, "operably linked" refers to sub-elements that function together in a unit, e.g., the linkage of regulatory elements such as a promoter DNA molecule, a transit peptide encoding DNA molecule, and a polyadenylation signal-encoding DNA molecule linked to transcribable DNA in a manner that the transcribable DNA is readily transcribed, translated, and functionally localized in a transgenic plant cell. In certain embodiments, such operably linked elements may be heterologous with respect to each other.

As used herein, "PI-PspI-RC" refers to the reverse complement of the restriction recognition site of the homing enzyme PI-PspI, and "I-SceI-RC" refers to the reverse complement restriction site of the homing enzyme I-SceI.

As used herein, "restriction endonuclease enzyme" refers to an enzyme (hereafter referred to as "restriction enzyme"), which has a distinct recognition sequence and cleavage pattern. The so-called recognition sequences are also referred to as "recognition sites" or "restriction sites." "Common restriction enzymes" and "common recognition sites" refer to restriction enzymes with restriction sites less than or equal to 6 nucleotides long that occur frequently. "Rare restriction enzymes" and their cognate "rare restriction sites" refer to restriction enzymes with cognate sequences greater than 6 nucleotides, and in one embodiment, greater than 8 nucleotides. The term "common" and "rare" are intended to refer to the frequency of occurrence of the restriction sites in a given genome. The statistical probability of the occurrence of a restriction site less than eight nucleotides long within a particular DNA molecule is much higher than the probability of the occurrence of a restriction site that is at least eight nucleotides long. As used herein, the term "unique" refers to any restriction endonuclease or HE site that is not found elsewhere within a DNA molecule. Restriction enzymes cut DNA sequences at a cleavage site, which might be identical or separate from the recognition site.

As used herein, "selected DNA" refers to a DNA segment which one desires to use for a particular purpose.

As used herein, "stack and stacking" refers to a vector comprising at least two gene expression cassettes (called a vector stack). The cassettes are stacked in a vector. The process of combining at least two gene expression cassettes into one vector is called stacking.

As used herein, "transcribable DNA" refers to a DNA molecule capable of being transcribed into an RNA molecule including, but not limited to, RNA that is translatable to a protein or polypeptide and RNA that is useful for gene suppression.

As used herein, "transformation construct" refers to a chimeric DNA molecule which is designed for introduction into a host genome by genetic transformation. Preferred transformation constructs will comprise all of the genetic elements necessary to direct the expression of one or more heterologous genes. In particular embodiments of the instant invention, it may be desirable to introduce a transformation construct into a host cell in the form of a gene expression cassette.

As used herein, "transformed cell" refers to a cell in which the DNA has been altered by the introduction of one or more heterologous DNA molecules into that cell.

As used herein, "transgene" refers to a segment of DNA which has been incorporated into a host genome or is capable of autonomous replication in a host cell and is capable of causing the expression of one or more RNAs and/or polypeptides. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

As used herein, "transgenic plant" or "transgenic organism" refers to a plant, progeny plant, organism, or progeny organism of any subsequent generation derived therefrom, wherein the DNA of the plant or organism or progeny thereof contains an introduced heterologous DNA segment not naturally present at that location in a non-transgenic plant or organism of the same variety. The transgenic plant or organism may additionally contain sequences which are native to the plant or organism being transformed, but wherein the gene has been altered in order to alter the level or pattern of expression of the gene, for example, by use of one or more heterologous regulatory or other elements.

As used herein, "vector" refers to a DNA molecule capable of replication in a host cell and/or to which another DNA segment can be operatively linked so as to bring about replication of the attached segment. A plasmid is an example of a vector. A vector is a construct designed for the introduction of heterologous DNA into a host cell. In this application, the words "vector," "plasmid," "plasmid vector," "transformation vector," and "construct" are used interchangeably.

Various embodiments of the present invention provide cloning vectors that will reduce the amount of manipulation needed to assemble gene expression cassettes into vectors. In certain aspects of the invention, the vector contains a multiple cloning site (MCS) with sets of rare restriction and/or HE sites arranged in a linear pattern that allows the stacking of cassettes in a directional and/or recursive way; eliminating the need to design special cloning vectors for each gene expression cassette, depending on the order and direction of this cassette in the vector stack. This is achieved by using homing enzymes that differ in their restriction sequences, but provide compatible ends to each other upon enzyme cleavage. For example, I-SceI and the reverse complement of PI-PspI (PI-PspI-RC) or, alternatively, PI-PspI and the reverse complement of I-SceI (I-SceI-RC) have this function. Only one vector for each cassette is needed to allow the introduction of the cassette anywhere in the vector stack. This arrangement defines a modular architecture that allows the user to assemble multiple cassettes into a single vector without disturbing the integrity of DNA elements already incorporated into the vector in previous cloning steps. The underlying basis for this stacking method is that the restriction site/sites used between individual cassettes are destroyed upon recombination, but are reintroduced into the vector stack by the fragment containing the cassette to be inserted into the stack and the vector that receives the cassette. Therefore, further stacking is enabled without interfering with cassettes that have already been added to the stack. When the I-SceI restriction site is used with the PI-PspI-RC restriction site to stack gene expression cassettes, SEQ ID NO:1 or 2 is located between, or adjacent these gene expression cassettes. Further, when the reverse complement of I-SceI restriction site is used with the PI-PspI restriction site to stack gene expression cassettes, SEQ ID NO:3 or 4 is generated and is located between or adjacent these gene expression cassettes.

An essential element in any cloning vector is a location for insertion of the genetic materials of interest. This is a synthetic element that has been engineered into "wild type" plasmids, thus conferring utility as a cloning vector. Any typical commercially-available cloning vector contains at least one such region, known as a multiple cloning site (MCS). A MCS typically comprises nucleotide sequences that may be cleaved by a single or a series of restriction enzymes, each of which has a distinct recognition sequence and cleavage pattern. The recognition sequences (which are also referred to as "restriction sites" or "recognition sites") in a DNA molecule often comprise a double-stranded palindromic sequence. For some restriction enzymes, as few as 4-6 nucleotides are sufficient to provide a recognition site, while some restriction enzymes require a sequence of 8 or more nucleotides. The enzyme NotI, for example, recognizes the octanucleotide sequence: 5' G-C-G-G-C-C-G-C 3', where 5' indicates the end of the molecule known by convention as the "upstream" end, and 3' likewise indicates the "downstream" end. The complementary strand of the recognition sequence would be its anti-parallel strand, 3' C-G-C-C-G-G-C-G 5'. Thus, the double stranded recognition site can be represented within the larger double-stranded molecule in which it occurs as:

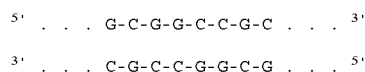

Like many other restriction enzymes, NotI does not cleave exactly at the axis of dyad symmetry, but at positions four nucleotides apart in the two DNA strands between the nucleotides indicated by a "/":

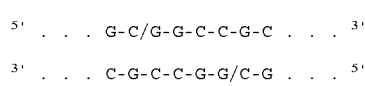

such that double-stranded DNA molecule is cleaved and has the resultant configuration of nucleotides at the newly formed "ends":

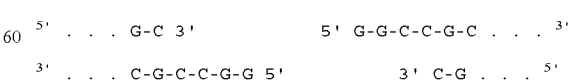

This staggered cleavage yields fragments of DNA with protruding 5' termini overhangs. Because A-T and G-C pairs are spontaneously formed when in proximity with each other, protruding ends such as these are called cohesive or sticky ends. Any one of these termini can form hydrogen bonds with any other complementary termini cleaved with the same restriction enzyme. Since any DNA that contains a specific recognition sequence site will be cut in the same manner as any other DNA containing the same sequence, those cleaved ends will be complementary. Therefore, the ends of any DNA molecules cut with the same restriction enzyme "match" each other in the way adjacent pieces of a jigsaw puzzle "match," and can be enzymatically connected (ligated) together. It is this property that permits the formation of recombinant DNA molecules, and allows the introduction of foreign DNA fragments into bacterial plasmids, or into any other DNA molecule. Another feature is that some restriction enzymes with different recognition sites still produce the same complementary ends upon cleavage. If DNA fragments are ligated that were cut by restriction enzymes harboring different restriction sites, but yielding complementary ends, the recombined sequence does often not serve as a restriction site for either restriction enzyme.

Some restriction enzymes cleave DNA within their recognition sequences. Most recognize DNA sequences that are symmetric, but a few recognize asymmetric DNA sequences. Some restriction enzymes recognize continuous sequences in which the two half-sites of the recognition site are adjacent, e.g., EcoRI: GAATTC. Other restriction enzymes recognize discontinuous sequences in which the half-sites are separated, sometimes by a degenerate sequence as is the case for SfiI.

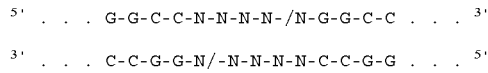

The "/" within this sequence marks the cleavage site. The degenerate nucleotide base symbol N is according to the IUPAC nomenclature representative for a position on a DNA sequence that can have multiple possible alternatives. N denotes any base, not a gap in the sequence. The degeneracy of the cleavage site can be used to design DNA sequences that are all recognized and cleaved by one restriction enzyme like SfiI, but that produce different overhangs upon cleavage, in this case 3' overhangs.

A further general principle to consider when building recombinant DNA molecules is that all restriction sites occurring within a molecule will be cut with a particular restriction enzyme, not just the site of interest. The larger a DNA molecule, the more likely it is that any restriction site will reoccur. Assuming that any restriction sites are distributed randomly along a DNA molecule, a tetranucleotide site will occur, on the average, once every $4^4$ (i.e., 256) nucleotides, whereas a hexanucleotide site will occur once every $4^6$ (i.e., 4096) nucleotides, and octanucleotide sites will occur once every $4^8$ (i.e., 114,688) nucleotides. Thus, it can be readily appreciated that shorter recognition sequences will occur frequently, while longer ones will occur rarely. When planning the construction of a transgene or other recombinant DNA molecule, this is a vital issue, since such a project frequently requires the assembly of several pieces of DNA of varying sizes. The larger these pieces are, the more likely that the sites one wishes to use occur in several pieces of the DNA components, making manipulation difficult, at best.

Frequently occurring restriction enzymes are herein referred to as "common restriction enzymes" and their cognate recognition sequences are referred to as common restriction sites. Restriction enzymes with cognate sequences greater than 6 nucleotides, particularly greater than 8 nucleotides are referred to as "rare" restriction enzymes, and their cognate sites as rare restriction sites.

A second class of restriction endonuclease enzymes has recently been discovered, called homing endonuclease (HE) enzymes. HE enzymes have large, asymmetric recognition sites (from 12-40 base pairs). HE recognition sites are extremely rare. For example, the HE known as I-SceI has an 18 bp recognition site (5'-TAGGGATAACAGGGTAAT-3', SEQ ID NO:5), predicted to occur only once in every $7 \times 10^{10}$ base pairs of random sequence. This rate of occurrence is equivalent to only one site in 20 mammalian-sized genomes. Another HE is PI-PspI with a 30-bp recognition site (5'-TGGCAAACAGCTATTATGGGTATTATGGGT-3', SEQ ID NO:6). Yet another HE is I-CeuI with a 29-bp long recognition site (5'-CGTAACTATAACGGTCCTAAGG-TAGCGAA-3', SEQ ID NO:7). The rare nature of HE sites greatly increases the likelihood that a genetic engineer can cut a final transgene product without disrupting the integrity of the transgene or the genome that comprises the transgene or the genome that comprises the transgene, if HE sites were included in appropriate locations in a cloning vector.

In certain embodiments of the current invention, the restriction sites used to stack two cassettes into one vector are eliminated upon recombination. If the restriction site for PI-PspI is reverse complemented (5'-ACCCATAATAC-CCATAATAGCTGTTTGCCA-3', SEQ ID NO:8) in the vector, the resulting overhang upon PI-PspI digestion is compatible with I-SceI (see FIG. 1). The resulting recombined sequence is not digested by either PI-PspI or I-SceI. Alternatively, the restriction site for I-SceI can be used in its reverse complement orientation (I-SceI-RC) to generate an overhang upon digestion with I-SceI that is compatible with the overhang generated by PI-PspI digestion of the PI-PspI restriction site. The reverse complement restriction site sequence of I-SceI is 5'-ATTACCCTGTTATCCCTA-3', SEQ ID NO:9.

Table 1 provides the sequences of restriction sites for some restriction enzymes used in embodiments of this invention. The direction of the sequences is from 5' to 3'.

TABLE 1

Restriction site sequences for restriction enzymes

| Restriction Enzyme | SEQ ID NO: | Restriction site sequence |
|---|---|---|
| I-SceI | 5 | TAGGGATAACAGGGTAAT |
| I-SceI-RC | 9 | ATTACCCTGTTATCCCTA |
| PI-PspI | 6 | TGGCAAACAGCTATTATGGGTATTATGGGT |
| PI-PspI-RC | 8 | ACCCATAATACCCATAATAGCTGTTTGCCA |
| CeuI | 7 | TAACTATAACGGTCCTAAGGTAGCGA |
| SrfI | | GCCCGGGC |
| PmeI | | GTTTAAAC |
| SwaI | | ATTTAAAT |
| AscI | | GGCGCGCC |
| SbfI | | CCTGCAGG |
| SfiI | 16 | GGCCNNNNNGGCC |

With a complex transgene, or with one that includes particularly large regions of DNA, there is an increased likelihood that there will be multiple recognition sites in these pieces of DNA. Recall that the recognition sequences encoding any one hexanucleotide site occur every 4096 bp. If a promoter sequence is 3000 bp and a gene of interest of 1500 bp are to be assembled into a cloning vector of 3000 bp, it is statistically very likely that many sites of six or less nucleotides will not be useful, since any usable sites must occur in only two of the pieces. Furthermore, the sites must occur in the appropriate areas of the appropriate molecules that are to be assembled. In addition, most cloning projects will need to have additional DNA elements added, thereby increasing the complexity of the growing molecule and the likelihood of inopportune repetition of any particular site. Since any restriction enzyme will cut at all of its sites in a molecule, if a restriction enzyme site reoccurs, all the inopportune sites will be cut along with the desired sites, disrupting the integrity of the molecule. Thus, each cloning step must be carefully planned so as not to disrupt the growing molecule by cutting it with a restriction enzyme that has already been used to incorporate a preceding element. Since most DNA constructs are designed for a single purpose, little thought is given to any future modifications that might need to be made, further increasing the difficulty for future experimental changes.

Traditionally, transgene design and construction consumes significant amounts of time and energy for several reasons, including the following:

1. There is a wide variety of restriction and HE enzymes available that will generate an array of termini, however most of these are not compatible with each other. Many restriction enzymes, such as NotI, generate DNA fragments with protruding 5' cohesive termini or "tails"; others (e.g., SbfI) generate fragments with 3' protruding tails, whereas still others (e.g., PmeI) cleave at the axis of symmetry to produce fragments with a blunt end. These protruding tails from either the 5' or 3' end are also called 3' or 5' overhangs. Other examples for overhang producing restriction enzymes are SfiI, SbfI, MreI, SgrAI, AsiSI. Further examples of blunt end producing restriction enzymes are SrfI and SwaI. An additional HE enzyme is I-PpoI. Some of these fragments with either an overhang or blunt end will be compatible with the termini formed by cleavage with other restriction and HE enzymes, but the majority of useful ones will not. The termini that can be generated with each DNA fragment isolation must be carefully considered in designing a DNA construct.

2. DNA fragments needed for assembly of a DNA construct or transgene must first be isolated from their source genomes, placed into plasmid cloning vectors, and amplified to obtain useful quantities. The step can be performed using any number of commercially-available or individually altered cloning vectors. Each of the different commercially available cloning vectors were, for the most part, developed independently, and thus contain different sequences and restriction sites for the DNA fragments of genes or genetic elements of interest. Genes must therefore be individually tailored to adapt to each of these vectors as needed for any given set of experiments. The same DNA fragments frequently will need to be altered further for subsequent experiments or cloning into other combinations for new DNA constructs or transgenes. Since each DNA construct or transgene is custom made for a particular application with no thought or knowledge of how it will be used next, it frequently must be "retrofitted" for subsequent applications.

3. In addition, the DNA sequence of any given gene or genetic element varies and can contain internal restriction sites that make it incompatible with currently available vectors, thereby complicating manipulation. This is true when assembling several DNA fragments into a single DNA construct, for example a promoter, gene of interest, and a terminator (3'UTR) into one gene expression cassette. This is especially true when assembling several gene expression cassettes into one vector, called a vector stack. In most transformation approaches, a single vector containing 1-2 genes conferring desirable characteristic(s) is introduced into a host of interest via an appropriate expression vector. Expression of a greater number of transgenes in host cells and organisms has proven to be costly and time consuming.

Figure 3:
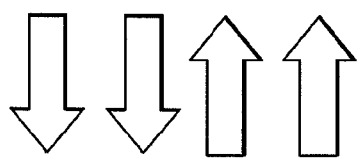
FIG. 3: Shows the four possible orientations of two gene expression cassettes. The arrow direction indicates the direction of the genetic expression elements in a cassette starting with the promoter and ending with the 3'UTR element.
Figure 3:
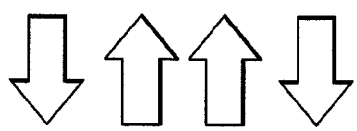

Rather than transforming one organism multiple times with vectors harboring individual gene expression cassettes it is of advantage to perform a single transformation event that inserts all gene expression cassettes in one vector into the organism in one step (U.S. Patent Publ. No. 2011/0099672). To achieve best efficacy of the expression of multiple gene expression cassettes in such vector stacks, it is necessary to test vectors that harbor these gene expression cassettes in different orientations and order. FIG. 3 demonstrates the possible orientation that two gene expression cassettes can have.

Therefore, the modular system of the current invention, allowing one to insert gene expression cassettes in a recursive directional stacking fashion by rare restriction sites within the cloning vector is especially useful.

The vector systems and methods available in the prior art necessitate the use of two types of vectors to achieve this flexibility. The first type harbors the individual gene expression cassettes with flanking regions that determine the assembly of multiple gene expression cassettes in the second type of vector, the so-called vector stack, in the desired order and orientation. Therefore one gene expression cassette might require the use of multiple vectors of the first type to yield the desired variety in the vector stacks. And such a system might be limited by the number of usable flanking regions in the number, order, and orientation these gene expression cassettes are assembled in the vector stack. Such flanking regions can be restriction sites, or attenuation sites for homologous recombination events.

Thus, the various embodiments of the instant invention that allow the user to rapidly assemble gene expression cassettes in any order, orientation, and number, into one vector, without the prerequisite to prepare the individual gene expression cassettes for the desired order in vectors first, are advantageous.

Transgene Expression Constructs

In various embodiments of the invention, transgene coding sequences operably linked to a promoter (e.g., a heterologous promoter) are provided, in either sense or antisense orientation. Expression constructs are also provided comprising these sequences, as are plants, seeds, and plant cells transformed with the sequences.

The construction of vectors which may be employed in conjunction with plant transformation techniques using these or other sequences according to the invention are known to those of skill of the art in light of the present disclosure (see, for example, Sambrook et al., 1989; Gelvin et al., 1990). Use of the various embodiments of the current invention are not limited to any particular nucleic acid sequences.

DNA segments used for transforming plant cells generally comprise RNA coding sequence, cDNA, gene, or genes which one desires to introduce into and have expressed in the host cells. These DNA segments can further include structures such as promoters, enhancers, polylinkers, regulatory genes, and/or any other sequence, as desired. The DNA segment or gene chosen for cellular introduction may encode a protein which will be expressed in the resultant recombinant cells, resulting in a screenable or selectable trait and/or which will impart an improved phenotype to the resulting transgenic plant. However, this may not always be the case, and various embodiments of the present invention also encompass transgenic plants incorporating non-expressed transgenes. Components likely to be included with vectors used in the current invention are listed in the following for exemplary purposes only and are not limited to those listed.

Regulatory Elements

Promoters for expression of a transgene may include, but are not limited to, plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those associated with the R gene complex (Chandler et al., 1989). Tissue-specific promoters such as root cell promoters (Conkling et al., 1990) and tissue-specific enhancers (Fromm et al., 1986) may also be useful, as are inducible promoters such as ABA- and turgor-inducible promoters. In certain aspects, a promoter for use according to the invention is a ePCISV, TubA, eFMV, FMV, e35S, 35S, or Ract1 promoter.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure.

It is specifically envisioned that transgene coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α or β-tubulin gene that also directs expression in roots.

Terminators

Transformation constructs prepared in accordance with the invention will typically include a 3' end DNA sequence that acts as a signal to terminate transcription and allow for the poly-adenylation of the mRNA produced by coding sequences operably linked to a transgene. Terminators which may be useful for this invention include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired. In certain aspects, a terminator for use according to the invention may be a Hsp17, TubA, Ara5, 35S, nos or Tr7 terminator.

Intron Sequences

In certain aspects, intron sequences are included in a gene expression cassette and may enhance transgene expression. In certain aspects, an intron for use according to the invention is a Ract1, TubA, Sus1, or Hsp70 intron.

Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids, and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

Marker Genes

By employing a selectable or screenable marker protein, one can provide or enhance the ability to identify transformants. "Marker genes" are genes that impart a distinct phenotype to cells expressing the marker protein and often provide a means to more efficiently distinguish such transformed cells from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea, or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Example Transgenes

Male Sterility

Examples of genes conferring male sterility include those disclosed in U.S. Pat. Nos. 3,861,709; 3,710,511; 4,654,465; 5,625,132; and 4,727,219, each of the disclosures of which are specifically incorporated herein by reference in their entirety. The use of herbicide-inducible male sterility genes is described in U.S. Pat. No. 6,762,344. Male sterility genes can increase the efficiency with which hybrids are made, in that they eliminate the need to physically emasculate plants used as a female in a given cross.

Herbicide Tolerance

Numerous herbicide resistance genes are known and may be employed with the invention. An example is a gene conferring resistance to a herbicide that inhibits the growing point or meristem, such as an imidazalinone or a sulfonylurea. Exemplary genes in this category code for mutant ALS and AHAS enzyme as described, for example, by Lee et al., (1988); Gleen et al., (1992); and Miki et al., (1990).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) may also be used. See, for example, U.S. Pat. No. 4,940,835 to Shah, et al., which discloses the nucleotide sequence of a form of EPSPS which can confer glyphosate resistance. Examples of specific EPSPS transformation events conferring glyphosate resistance are provided by U.S. Pat. No. 6,040,497.

Disease and Pest Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., (1994) (cloning of the tomato Cf-9 gene for resistance to *Cladosporium fulvum*); Martin et al., (1993) (tomato Pto gene for resistance to *Pseudomonas syringae* pv.); and Mindrinos et al., (1994) (*Arabidopsis* RSP2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses (see Beachy et al., 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

Insect Resistance

One example of an insect resistance gene includes a *Bacillus thuringiensis* protein, a derivative thereof, or a synthetic polypeptide modeled thereon. See, for example, Geiser et al., (1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example of insect resistance gene which could be used for the present invention is a lectin. See, for example, Van Damme et al., (1994), who disclose the nucleotide sequences of several *Clivia miniata* mannose-binding lectin genes. A vitamin-binding protein may also be used, such as avidin (see PCT application US93/06487, the contents of which are hereby incorporated by reference). This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., (1987) (nucleotide sequence of rice cysteine proteinase inhibitor), Huub et al., (1993) (nucleotide sequence of cDNA encoding tobacco proteinase inhibitor I), and Sumitani et al., (1993) (nucleotide sequence of *Streptomyces nitrosporeus* α-amylase inhibitor). An insect-specific hormone or pheromone may also be used. See, for example, the disclosure by Hammock et al., (1990), of baculovirus expression of cloned juvenile hormone esterase, an inactivator of juvenile hormone.

Antisense and RNAi Constructs

A transgene for use according to the invention may also comprise an antisense or RNAi coding sequence.

Plant Transformation and Breeding

Methods for transformation of plants are known in the art. Suitable methods of transforming plant cells include microinjection (Crossway et al. (1986) *Biotechniques* 4:320-334), electroporation (Riggs et al. (1986) *Proc. Natl. Acad. Sci. USA,* 83:5602-5606), *Agrobacterium* mediated transformation (Hinchee et al. (1988) *Biotechnology,* 6:915-921), direct gene transfer (Paszkowski et al. (1984) *EMBO J.,* 3:2717-2722), and ballistic particle acceleration (see, for example, Sanford et al., U.S. Pat. No. 4,945,050; WO 91/10725 and McCabe et al. (1988) Biotechnology, 6:923-926); all of which are herein incorporated by reference.

After effecting delivery of exogenous DNA to recipient cells via transformation, the next steps concern identifying the transformed cells for further culturing and plant regeneration. In order to improve the ability to identify transformants, one may desire to employ a selectable or screenable marker gene with a transformation vector prepared in accordance with the invention. In this case, one would then assay the potentially transformed cell population by exposing the cells to a selective agent or agents, or one would screen the cells for the desired marker gene trait.

Cells that survive the exposure to the selective agent, or cells that have been scored positive in a screening assay, may be cultured in media that supports regeneration of plants.

To confirm the presence of the exogenous DNA or "transgene(s)" in the regenerating plants, mature plants, plant tissue and plant seeds, a variety of assays may be performed. Such assays include, for example, molecular biological assays, such as Southern and northern blotting and PCR; biochemical assays, such as detecting the presence of a protein product, e.g., by immunological means (ELISA and western blotting), or by enzymatic function; plant part assays, such as leaf or root assay; and also, by analyzing the phenotype of the whole regenerated plant.

These regenerated plants may then be pollinated with either the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

EXAMPLES

The following examples provide illustrative embodiments of the invention. However, those of skill in the art should, in light of the present disclosure, appreciate that many changes can be made in specific aspects of these embodiments without departing from the concept, spirit, and scope of the invention. Moreover, it is apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims. The following examples use the pair of PI-PspI-RC and I-SceI restriction sites to stack gene expression cassettes in a vector. A combination of PI-PspI and I-SceI-RC restriction sites can alternatively be used to stack genes and are exemplified in examples 13 and 14.

Example 1

Assembly of a Gene Expression Cassette in a Vector

This example illustrates the fabrication of individual gene expression elements, e.g., promoter, GOI, and 3' UTR, into one gene expression cassette (cas) in a vector useful for transformation. The following methods are related to a gene expression cassette containing three elements, but a person skilled in the art will be able to use this method to assemble gene expression cassettes comprising 4, 5, or more elements to account for enhancer, intron, 5' leader, signaling peptides, and other gene expression elements.

Bacterial Strains and Growth Conditions. Plasmids were introduced into *Escherichia coli* by either electroporation or by chemical transformation. The following *E. coli* strains were used: DH10B [genotype: F$^-$ mcrA Δ(mrr-hsdRMS-mcrBC) φ80dlacZΔM15 ΔlacX74 deoR relA1 araD139 Δ(ara leu)7697 galU galK rpsL endA1 nupG] (Invitrogen, CA) and NEB 10-beta [genotype: araD139 Δ(ara,leu)7697 fhuA lacX74 galK16 galE15 mcrA f80d(lacZΔM15)recA1 relA1 endA1 nupG rpsL rph spoT1Δ(mrr-hsdRMS-mcrBC)] (New England Biolabs, Boston, Mass.). Cells were propagated in LB medium (Luria-Bertani) containing the appropriate antibiotics.

Enzymes and Reagents. Unless otherwise noted, DNA polymerases used in the process were from New England Biolabs (Boston, Mass.), Promega (Madison, Wis.), Fermentas (Glen Burnie, Md.), Invitrogen (Carlsbad, Calif.), or Stratagene (La Jolla, Calif.). DNA and PCR product purification kits were from Qiagen (Hilden, Germany) or Zymo Research Corp (Orange, Calif.). Chemicals, such as Tris, EDTA, and NaCl, and antibiotics were from Sigma (St. Louis, Mo.). All other consumables, e.g., PCR plates, tubes, and tips, were from VWR (West Chester, Pa.).

PCR. Amplifications were performed in 50-μl total volume reactions containing 5.0 μl of 10×PCR buffer, 1.0 μl of dNTPs (10 mM), 1.0 μl of 5' primer oligo (10 μM), 1.0 μl of 3' primer oligo (10 μM), 1.0 μl of KOD Hot Start DNA Polymerase™ (2 U/μl), 1 μl of DNA template [for plasmid DNA (~1 ng/μl), and for cDNA or gDNA (~50 ng/μl)], and sterile water to 50 μl. The PCR cycling program was as follows: Step 1: 95° C. for 2 min; step 2: 95° C. for 20 sec; step 3: 58° C. for 20 sec; step 4: 70° C. for 3 min; step 5: go back to step 2 for 24 cycles; step 6: 70° C. for 5 min and step 7: hold at 10° C. The PCR products were purified via column or gel, or directly used for subsequent steps.

Primer Design and Sequencing Analysis. DNA analysis and design of primers used for PCR and sequencing were done by DNA Star software (DNASTAR Inc., Madison, Wis.). Stitch PCR is based on the introduction of overlapping sequences to the individual elements by using appropriate PCR primers. The nature of these overlapping sequences determines the order of the elements in the gene expression cassette.

$1^{st}$ PCR. The $1^{st}$ PCR was performed with gene-specific primers in a 50-μl reaction containing 5.0 μl of 10×PCR buffer, 1.0 μl of dNTPs (10 mM), 1.0 μl of 5' F1 primer oligo (10 μM) (F1 for $1^{st}$ fragment, F2 for 2nd fragment, F3 for $3^{rd}$ fragment, etc.), 1.0 μl of 3' R1 primer oligo (10 μM) (R1 for $1^{st}$ fragment, R2 for 2nd fragment, R3 for $3^{rd}$ fragment, etc.), 1.0 μl of KOD Hot Start DNA Polymerase (2 U/μl), 1 μl of DNA template (for plasmid DNA, ~1 ng/μl, and for cDNA or gDNA, ~50 ng/μl), and sterile water to 50 μl. The PCR cycling program was the same as mentioned above, except 15 cycles of amplification were performed in total. The first PCR products can be column or gel-purified or directly used as template for the second PCR.

$2^{nd}$ PCR for Gene Assembling. The $2^{nd}$ PCR for gene assembly was carried out in a 50-μl reaction containing 5.0 μl of 10×PCR buffer, 1.0 μl of dNTPs (10 mM), 1.0 μl of the $1^{st}$ PCR product for the first fragment, 1.0 μl of the $1^{st}$ PCR product for the second fragment, 1.0 μl of the $1^{st}$ PCR product for the third fragment, 1.0 µl of F1 primer oligo, 1.0 µl of R3 primer oligo, 1.0 µl of KOD Hot Start DNA Polymerase (2 U/µ1), and sterile water to 50 µl. The PCR cycling program was as follows: $1^{St}$ step: 95° C. for 2 min; 2nd step: 95° C. for 30 sec; 3rd step: 55° C. for 3 min; 4th step: 68° C. for 3 min; 5th step: go back to step 2 for 14 cycles; 6th step: 70° C. for 5 min and 7th step: hold at 10° C. For assembly of three fragments, F1 and R3 primer oligos were used for the $2^{nd}$ PCR.

The $2^{nd}$ PCR product (assembled full-length expression cassette) was gel-purified as described above, and then digested with restriction enzymes for conventional cloning into the vector.

AscI/SfiI Based Multi-Fragment Assembling. Alternatively, gene expression elements can be assembled using a restriction endonuclease approach as described by U.S. Pat. No. 5,595,895, hereby incorporated by reference in its entirety.

Figure 4:
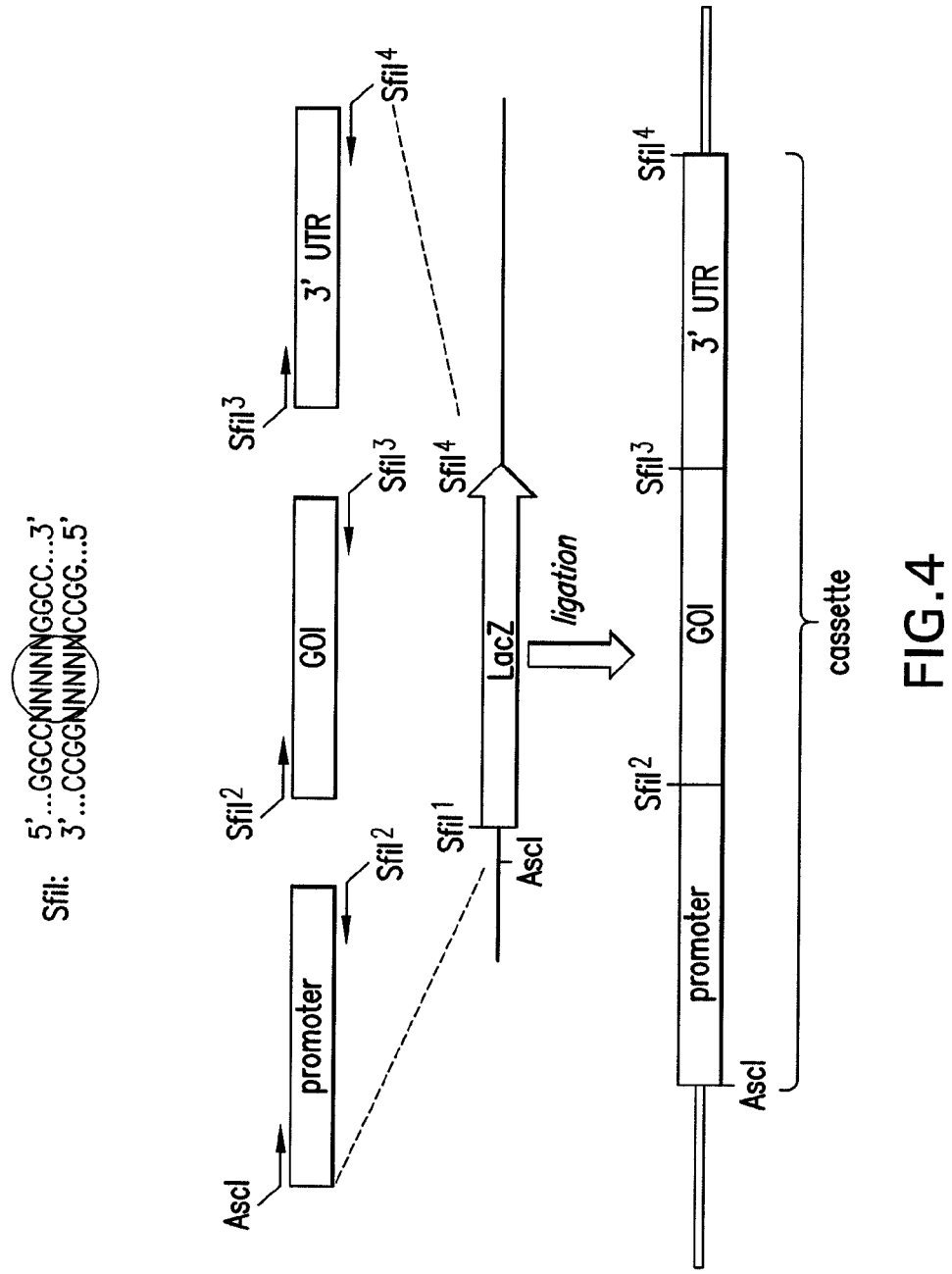
FIG. 4: Shows how a gene expression cassette can be assembled using the restriction enzymes AscI and SfiI taking advantage of the degenerate sequence within the SfiI cutting site. In this case, the gene expression cassette contains a promoter, a gene-of-interest (GOI), and a transcription terminator (3'UTR).

Using AscI in addition to SfiI lowers the risk of self-annealing of the vector and drives the cloning efficiency, since AscI generates a 5' overhang, whereas SfiI generates a 3' overhang. AscI and SfiI both recognize 8-bp unique sequences, but SfiI contains a 5-bp degenerate sequence in the recognition site. The cleavage site of SfiI enzyme is located in the degenerate region, leading to unique 3-bp 3' overhangs useful for directional cloning (FIG. 4).

The elements, e.g., promoter, GOI, and 3'UTR, were PCR-amplified with primers containing gene expression element-specific sequences and unique SfiI sequences that enabled the incorporation of these unique SfiI sequences on both sides of the PCR-amplified elements, and determined the order of the elements in the assembled gene expression cassette. The uniqueness of these SfiI sequences is in the degenerate sequence of the SfiI restriction site, as indicated by $SfiI^1$, $SfiI^2$, $SfiI^3$, and $SfiI^4$ in FIG. 4. The following adaptors (containing the gene expression element-specific sequences and restriction enzyme-specific sequences) were commonly used for amplification of each element: 5' promoter adaptor containing AscI site (ctgctt ggcctactaggccggcgcgcc) (SEQ ID NO:10), 3' promoter adaptor containing $SfiI^2$ site (ggtacctggccagtctggcctcggtccg) (SEQ ID NO:11), 5' GOI adaptor containing $SfiI^2$ site (cggaccgaggccagactggccaggtacc) (SEQ ID NO:12), 3' GOI adaptor containing $SfiI^3$ site (gggccctggccacagtggccttaattaa) (SEQ ID NO:13), 5' 3' UTR adaptor containing $SfiI^3$ site (ttaattaaggccactgtggccagggccc) (SEQ ID NO:14) and 3' 3'UTR adaptor containing $SfiI^4$ site (gctcgt ggccgtcacggccacctgcagg) (SEQ ID NO:15). The restriction enzyme-specific sequences are underlined. The sequence of $SfiI^4$-containing adaptor matched that of the $SfiI^4$ site on the vector. $SfiI^1$, $SfiI^2$, $SfiI^3$, and $SfiI^4$ sites here have different sequences in the degenerate region (see FIG. 4).

The PCR-amplified promoter element was digested with AscI and SfiI, while the GOI and 3'UTR elements were digested with SfiI only. Ligation with T4 DNA ligase was then set up with the three restriction enzyme-digested fragments and AscI/SfiI-digested vectors. The three fragments were cloned in the order of promoter-GOI-3' UTR as expected.

Example 2

Construction of a Double Gene Expression Cassette Vector

Figure 5:
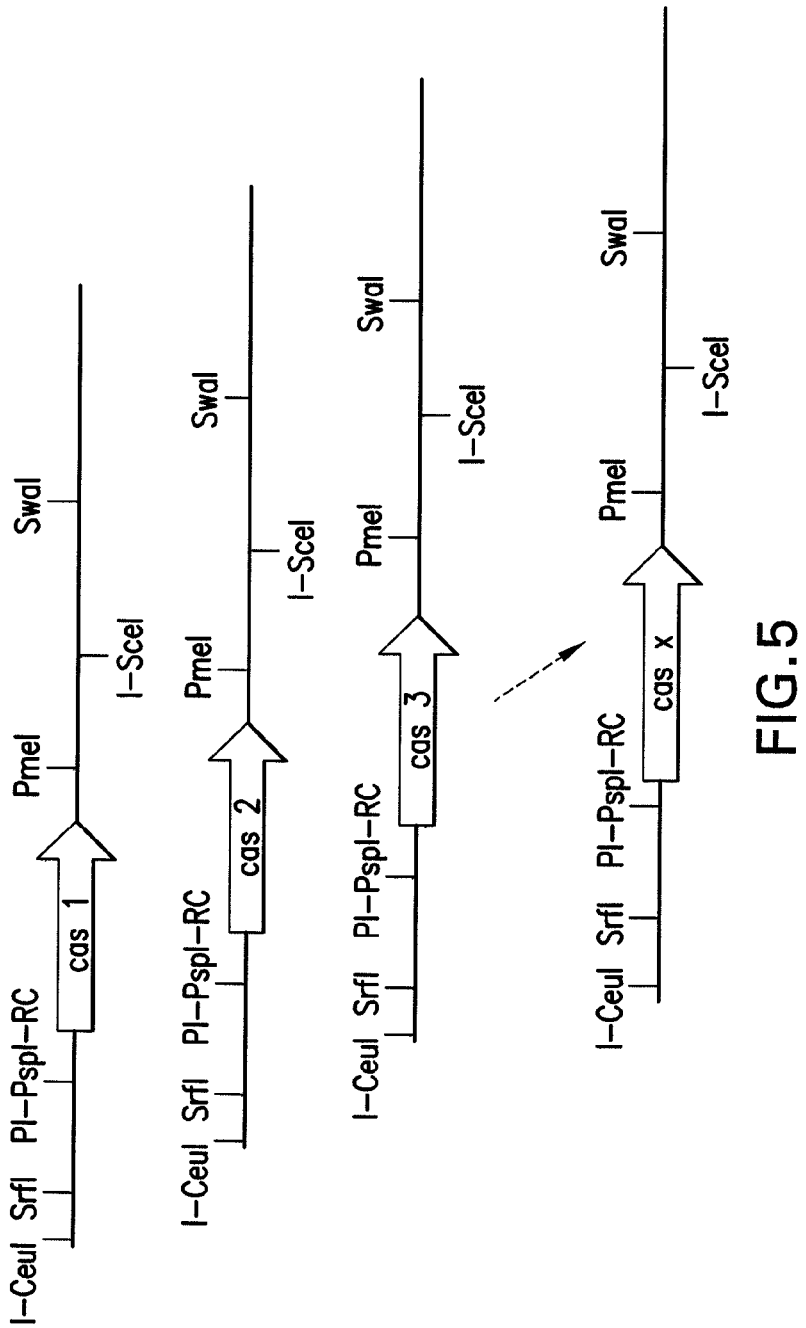
FIG. 5: Shows an example where the individual vectors used for all gene expression cassettes are identical. In this case, an identical multiple cloning site (MCS) with vector-a of FIG. 6 is used. Every vector contains a single gene expression cassette.
Figure 6:
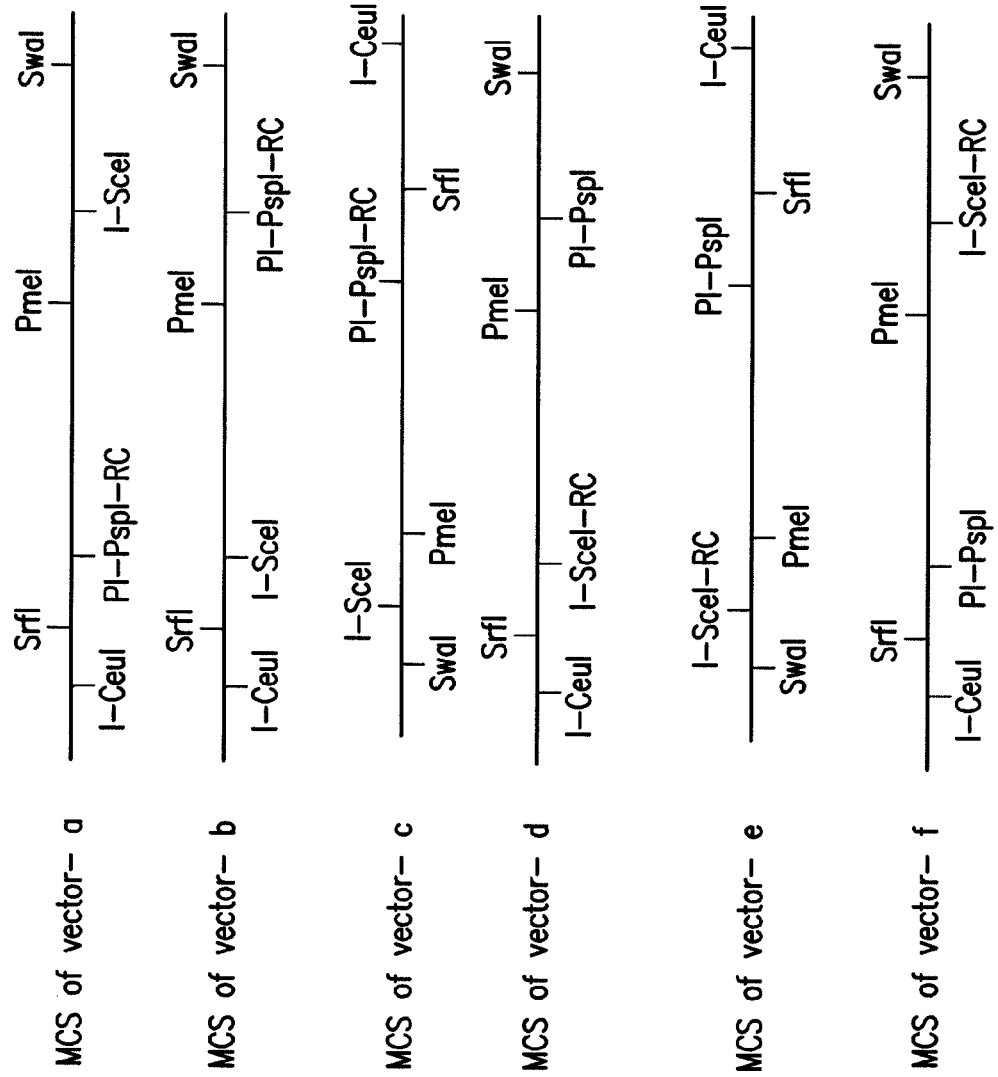
FIG. 6: Shows three non-limiting examples of the possible designs for the MCS of a vector of the present invention comprising the I-SceI restriction site and the reverse complemented restriction site for PI-PspI. An additional three non-limiting examples are shown for vectors comprising the PI-PspI restriction site and the reverse complemented I-SceI restriction site.

This method was based on all gene expression cassettes being present in the same type of vector as shown in FIG. 5 and FIG. 6 (either in MCS a, b, or c configuration). Cassettes could be added to an existing vector or vector stack either downstream (3'-terminal) or upstream (5'-terminal) of the cassette or cassettes already present in the vector stack. The process of adding cassettes to the stack down- or upstream could be repeated in unlimited fashion in theory and is limited in practice by the size of the vector that can still be successfully used for transformation. The principle is the following: One restriction site is used to cut both the vector to isolate the DNA fragment that contains the cassette to be added, and the vector that will accept this cassette. This restriction site is retained upon recombination to generate the vector stack and thus is available for putative subsequent stacking. The second restriction site used is different for the isolation of the DNA fragment containing the cassette (site 2a, I-SceI site in FIG. 7) and the vector that the cassette is inserted into (site 2b, PI-PspI-RC site in FIG. 7). The two different restriction enzymes, now called restriction enzyme 2a and restriction enzyme 2b for exemplary purposes, still generate compatible ends and, upon assembly of the vector stack, this recombined site is not recognized by either restriction enzyme 2a or restriction enzyme 2b. However, due to the design of the vector, restriction sites 2a and 2b are still present in the vector stack, since restriction site 2a is still present in the vector used for stacking (highlighted in a star), and restriction site 2b gets reintroduced into the vector stack by the DNA fragment that contains the cassette to be added (highlighted in a star). This method is shown in more detail in FIG. 7. Restriction enzymes used for stacking are circled in the figures, and restriction sites that are reintroduced to the vector stack are highlighted in a star. Only restriction enzymes that are unique, occurring only once in the vector stacks are shown.

Figure 7:
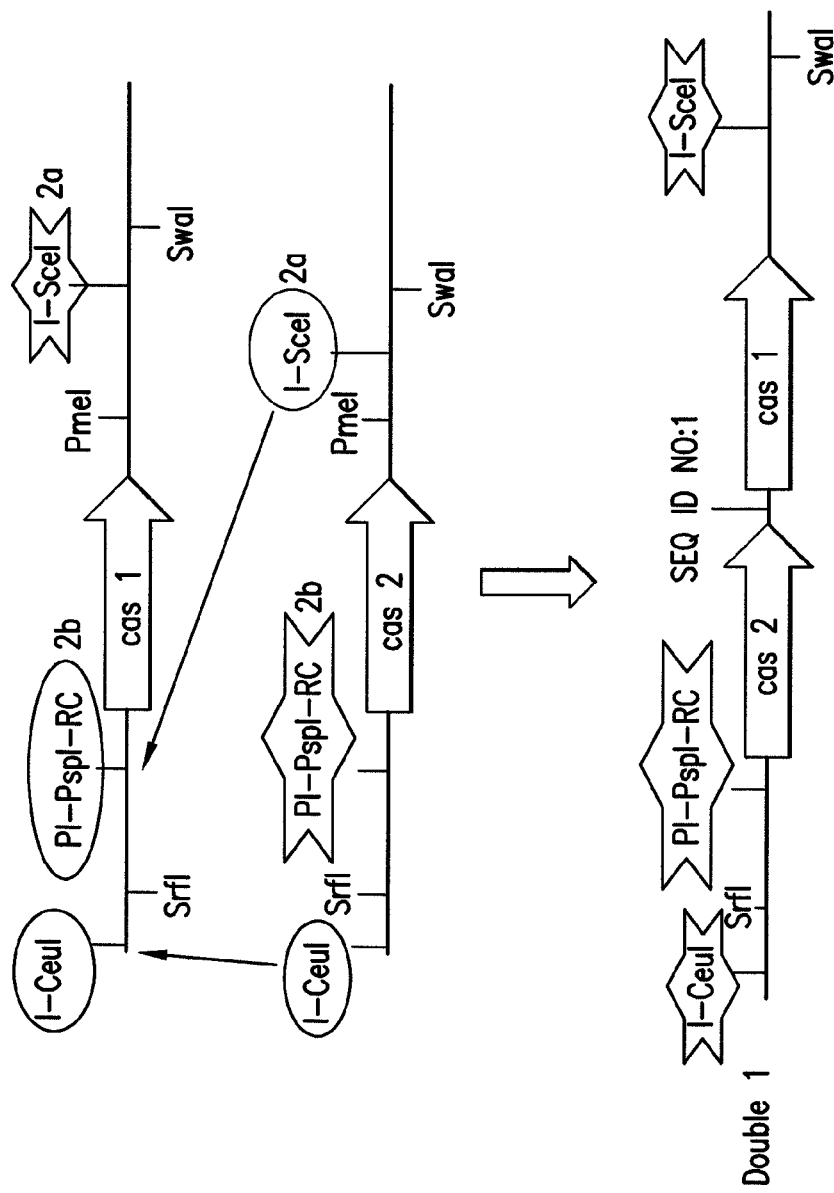
FIG. 7: Shows stacking of cassette 2 (cas 2) upstream of cassette 1 (cas 1) generating a double-vector stack (Double 1). The restriction sites used are circled. Of these restriction sites, those that are available for further stacking approaches are marked in a star. The recombined restriction site of I-SceI and PI-PspI-RC is also shown. This recombined site is not available for digestion with either restriction enzyme and is located between gene expression cassette 2 and gene expression cassette 1 (indicated by SEQ ID NO:1).

As shown in FIG. 5, once the single gene cassettes were made using the same modular vector, the fragment containing the second gene cassette, cas 2 in FIG. 7, was isolated by digestion of the construct with I-CeuI and I-SceI for 2 hrs at 37° C. in a 30-µl reaction containing 2 µg of the vector DNA, 2 µl of each enzyme (10 U/µ1), 3 µl of 10× NEBuffer-4, and adjusted with sterile water to a total volume of 30 µl. The expected fragment containing cassette 2 was gel-purified. The vector containing the first gene expression cassette (cas 1 in FIG. 7) was then linearized by sequential digestion with I-CeuI and PI-PspI in a 30-µl reaction mixture containing 2 µg of the vector DNA, 2 µl of I-CeuI, 3 µl of 10× NEBuffer-4, and adjusted with sterile water to a total volume of 30 µl at 37° C. for 1 hr, followed by two additional hours of incubation at 37° C. after the addition of 2 µl of PI-PspI and 3 µl of NEBuffer PI-PspI. When the digestion was complete, gel-purification of the desired vector fragment and ligation of cassette 2 into the linearized vector containing cassette 1 was performed in a 10-µl ligation reaction containing 50 ng of linearized vector DNA, 10-20 ng of isolated insert DNA containing cassette 2, 1 µl of T4 DNA ligation buffer, 0.5 µl of T4 DNA ligase (20 U/µl, NEB cat. #M0202S) and sterile water. The ligation mixture was kept at 16° C. for 12-20 hrs followed by heat-inactivation of the ligase at 65° C. for 15 min. One microliter of the ligation mix was used to transform 20 µl of DH10B competent cells and plated on plates containing appropriate antibiotic selection. After overnight incubation of the plates, colonies harboring the plasmid containing the putative double-stacked cassettes were screened using colony-PCR screening. Plasmid DNAs were obtained from PCR-positive clones for restriction enzyme digestion confirmation, and the putative constructs were verified by sequencing.

I-CeuI and PI-PspI were used to linearize the vector, and I-CeuI and I-SceI were used to isolate the fragment containing cassette 2. Upon integration of the cassette 2-containing fragment into the linearized vector containing cassette 1, the I-CeuI recognition site was retained, but the PI-PspI-RC site of the vector with cassette 1 and the I-SceI site of the vector with cassette 2 were lost. However, since the vector with cassette 1 still contained a I-SceI recognition site (highlighted with a star box in FIG. 7), and the vector with cassette 2 still contained a recognition site for PI-PspI-RC (also highlighted with a star box in FIG. 7), both recognition sites for I-SceI and PI-PspI-RC were still present in the double-stack vector with cassette 1 and cassette 2 and all three recognition sites (I-CeuI, I-SceI and PI-PspI-RC) could be used for adding more cassettes according to the same principle. Only restriction and HE sites that were unique in the vector and available for additional stacking steps are shown in FIG. 7.

The order of cassettes 1 and 2 in the double-stack vector could be reversed by isolating cassette 1 and inserting it into the linearized vector with cassette 2.

Example 3

Construction of Two Double-gene Stack Vectors

Figure 8:
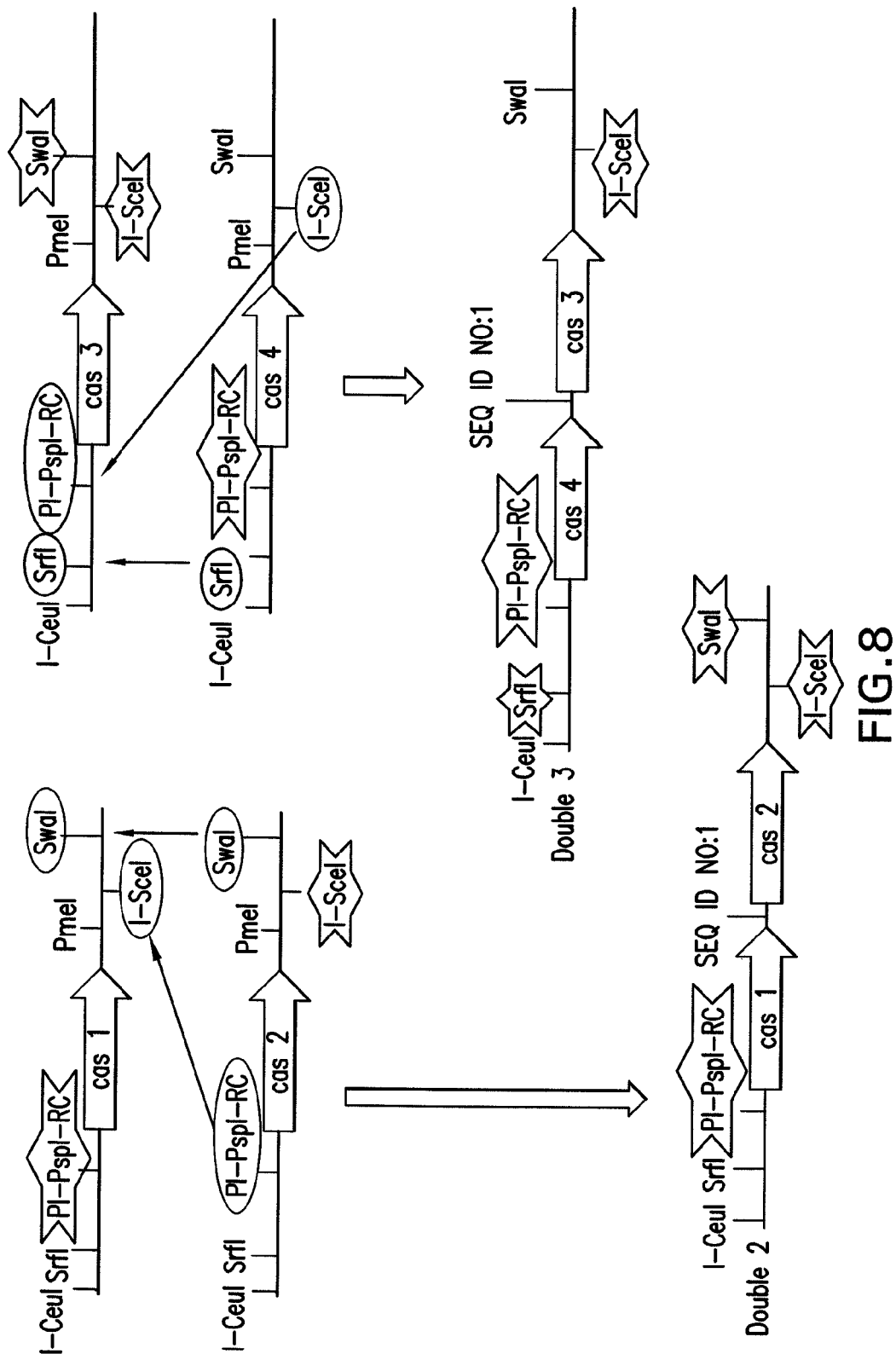
FIG. 8: Shows the stacking of cassette 2 downstream of cassette 1 using the vector of cassette 1 to generate the vector stack Double 2; and the stacking of cassette 4 upstream of cassette 3 using the vector of cassette 3 to produce the vector stack Double 3. The restriction sites used for the generation of both double-stack vectors are shown in circles. Of these restriction sites, those available for further stacking purposes are shown in a star. The recombined restriction site of I-SceI and PI-PspI-RC is also shown (SEQ ID NO:1). This recombined site is not available for digestion with either restriction enzyme and is located between gene expression cassette 1 and gene expression cassette 2 of the vector stack Double 2 and between gene expression cassette 4 and gene expression cassette 3 of the vector stack Double 3.

Instead of using an all homing enzyme approach (I-CeuI, PI-PspI, I-SceI) as shown in Example 2 and FIG. 7, a blunt-end cutter (SwaI or SrfI) can be used for adding another cassette downstream or upstream of a cassette already contained in a vector. FIG. 8 demonstrates the construction of two double-stack vectors. Double 2 is a vector containing cassette 1 and cassette 2 and is generated by linearizing the vector containing cassette 1 with I-SceI and SwaI and inserting a fragment containing cassette 2 that is produced by isolation with SwaI and PI-PspI digestion. Since sites for SwaI, I-SceI, and PI-PspI-RC are still present in the assembled two-cassette stack vector, additional cassettes can be added. Double 3 is a vector containing cassette 4 and cassette 3 and is generated by linearizing the vector containing cassette 3 with SrfI and PI-PspI and inserting a fragment containing cassette 4 that is produced by isolation with SrfI and I-SceI digestion. Again, Double 3 contains SrfI, PI-PspI-RC, and I-SceI restriction sites and can be used for additional cassette stacking. In both examples for Double 2 and Double 3, the restriction site between the two cassettes is destroyed, since recombination sequences of I-SceI and PI-PspI-RC are not recognized by enzymes used in this invention, but these sites are reintroduced into the double-stack vector by the respective recognition sites of the linearized vector, as well as the cassettes containing isolated fragment (highlighted by a star box in FIG. 8). Destruction of the recognition sites between stacked cassettes allows progressive addition of more cassettes either downstream or upstream of the cassettes already in the vector and also protects against unwanted cleavage between individual cassettes.

Example 4

Construction of a Four Gene Expression Cassette Vector Stack

Figure 9:
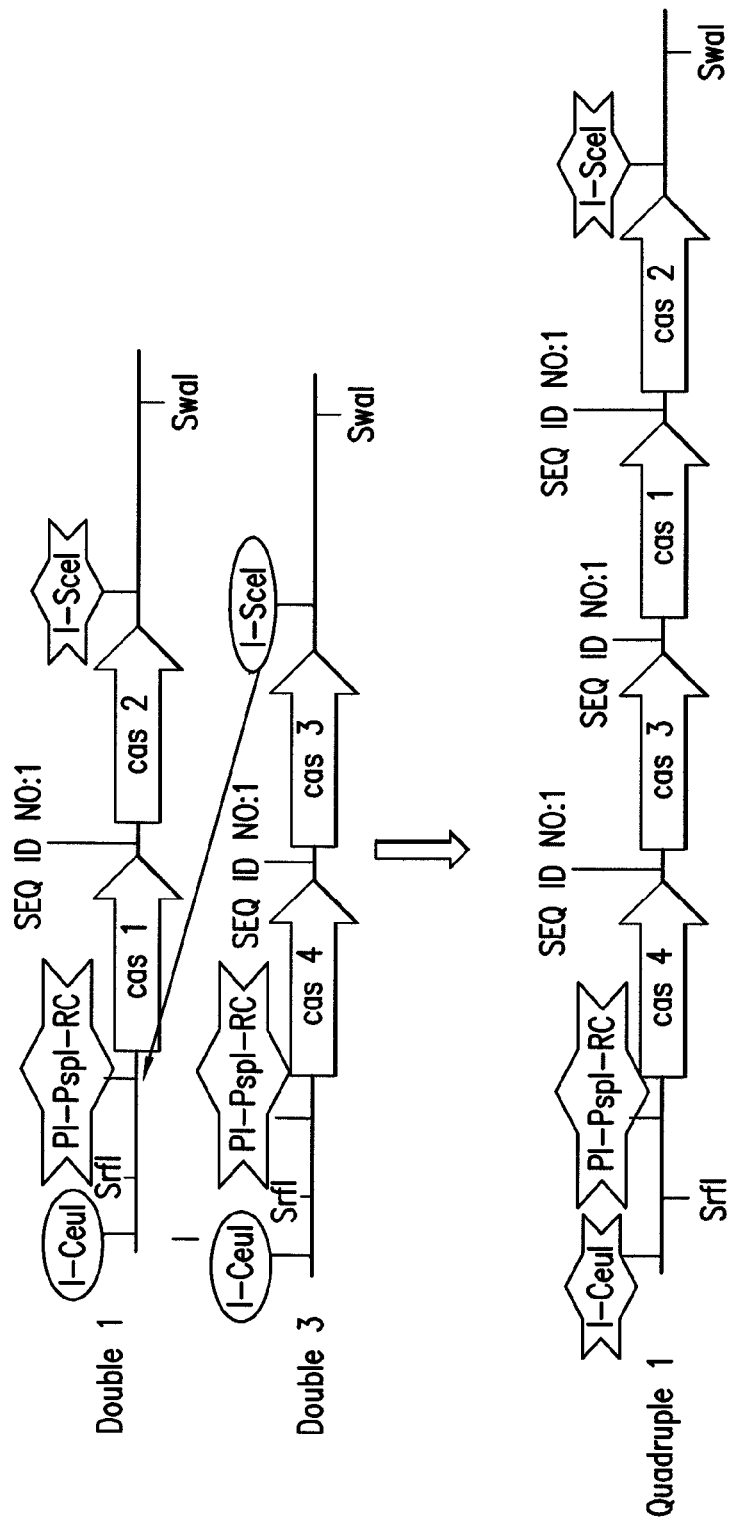
FIG. 9: Shows how the two cassettes isolated from Double 3 can be added upstream of the two cassettes from Double 2 to create a four-cassette vector stack. The restriction sites used for the generation of the four-cassette vector stack are shown in circles. Of these restriction sites, those available for further stacking purposes are shown in a star. The recombined restriction site of I-SceI and PI-PspI-RC is also shown. This recombined site is not available for digestion with either restriction enzyme and is located between gene expression cassettes 4 and 3, between gene expression cassettes 3 and 1, and between gene expression cassettes 1 and 2.

The two-cassette vector stacks Double 1, Double 2, and Double 3 can be further combined. FIG. 9 shows the generation of a four-cassette vector stack (Quadruple 1) using Double 2 and Double 3. Double 2 is linearized by digestion with both I-CeuI and PI-PspI. Cassettes 4 and 3 are isolated from Double 3 by digestion with I-CeuI and I-SceI. Recombination of linearized vector and cassette fragment produces a four-cassette vector stack that can be further used to stack additional cassettes.

Example 5

Construction of a Vector Stack with Head-to-head Orientation of Two Cassettes

Figure 10:
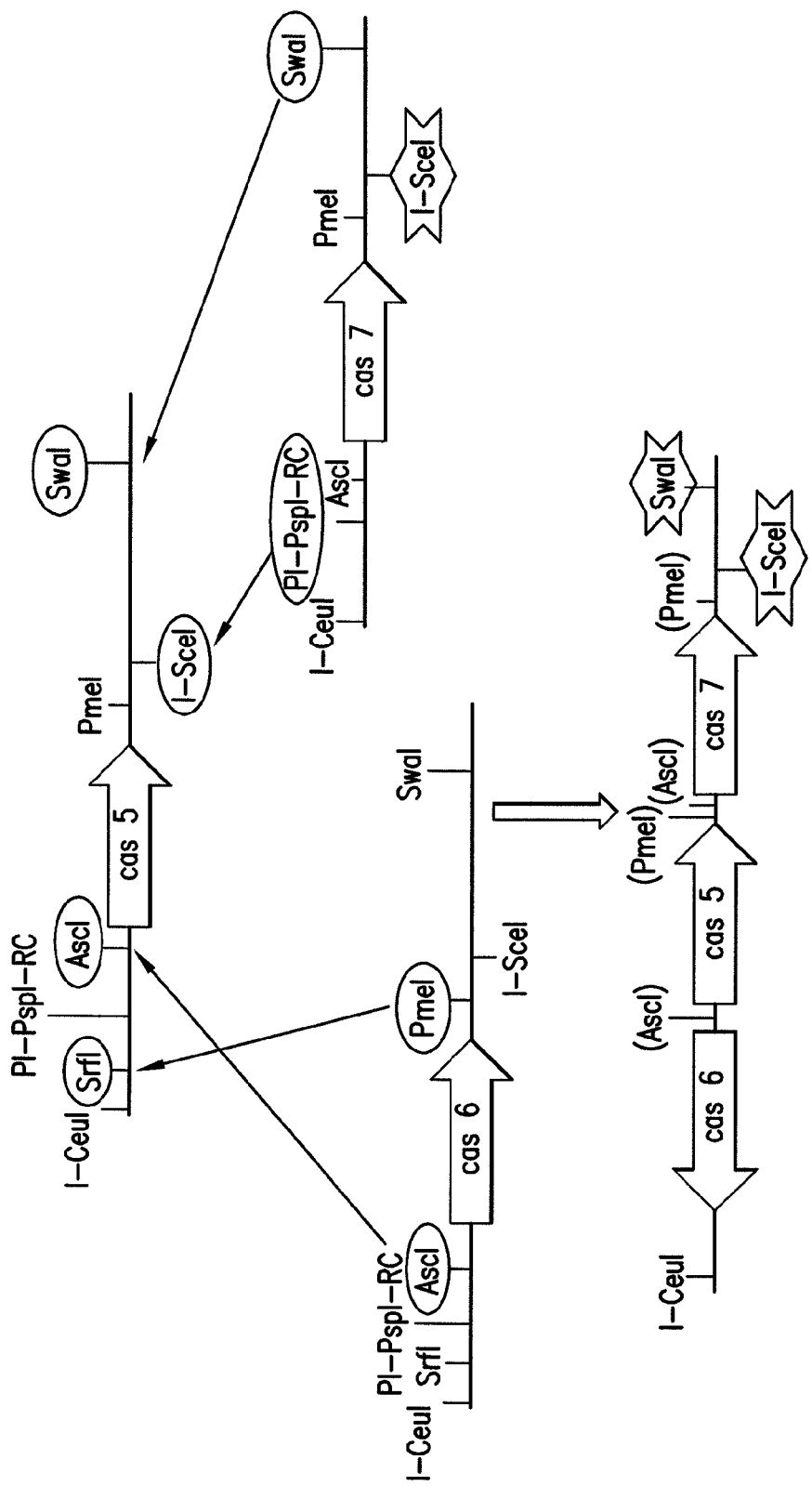
FIG. 10: Shows that cassettes can be stacked in head-to-head orientation and still be utilized for further stacking. Introduction of cassettes 6 and 7 to a vector with cassette 5 is done in subsequent reactions. The restriction sites used for the generation of the vector stacks are shown in circles. Of these restriction sites, those available for further stacking purposes are shown in a star. The restriction site for AscI and also for PmeI is set in parentheses to show that these two sites are not used for further stacking purposes, since they are no longer unique.

FIG. 10 demonstrates how one cassette (here cassette 6) can be added to a vector stack in reversed orientation, resulting in head-to-head orientation of two neighboring cassettes by taking advantage of the AscI site that was used to assemble the gene expression cassette in the vector (see Example 1 and FIG. 4). The vector with cassette 5 is linearized with SrfI and AscI, and cassette 6 is isolated by digestion with AscI and PmeI. Recombination of linearized vector and isolated cassette leads to a head-to-head orientation of cassette 6 to cassette 5. The resulting double-stack can be further used for additional stacking as shown in FIG. 10 by adding cassette 7 downstream to cassette 5 using I-SceI and SwaI to linearize the double-stack vector and PI-PspI and SwaI to isolate the DNA fragment containing cassette 7. Additional stacking downstream of cassette 7 is possible. In addition, the entire three-cassette stack could be isolated by digestion with I-CeuI and I-SceI and could be used for insertion into another vector of this invention. However, the AscI site of the above described two- and three-cassette vector stacks is now located between two cassettes (cas 6 and cas 5, as well as cas 5 and cas 7), and the PmeI site is now located upstream and downstream of cassette 7. Both AscI and PmeI are unavailable for further stacking purposes, since the both sites now appear more than once in the vector and are thus no longer unique.

Figure 11:
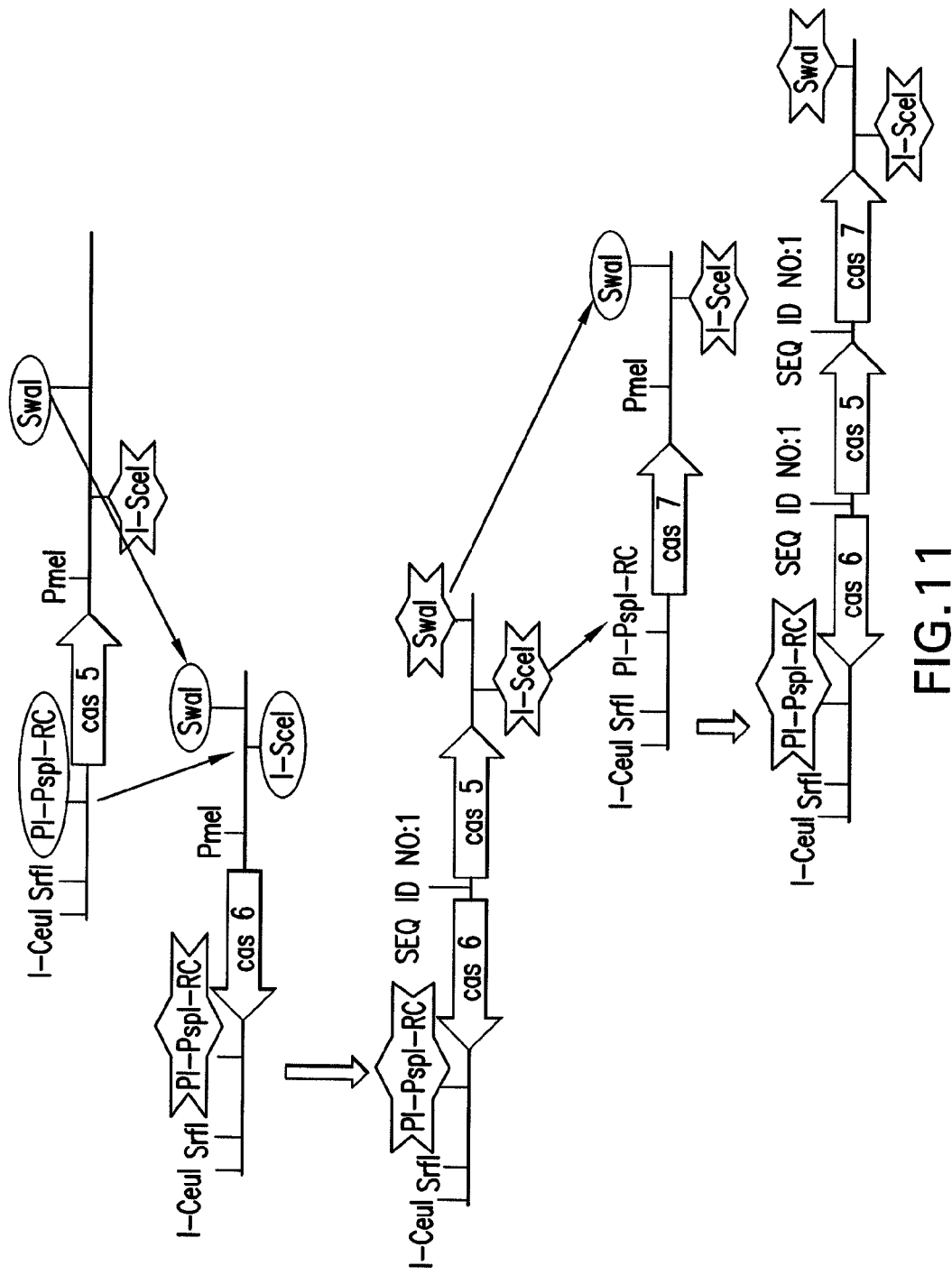
FIG. 11: Shows an alternate triple-stack vector in head-to-head and tail-to-head orientations.

It is contemplated in this invention that cassettes might be assembled in reverse orientation in the vector, thus achieving head-to-head or tail-to-head orientation without the loss of restriction sites for further stacking purposes (FIG. 11).

Example 6

Figure 12:
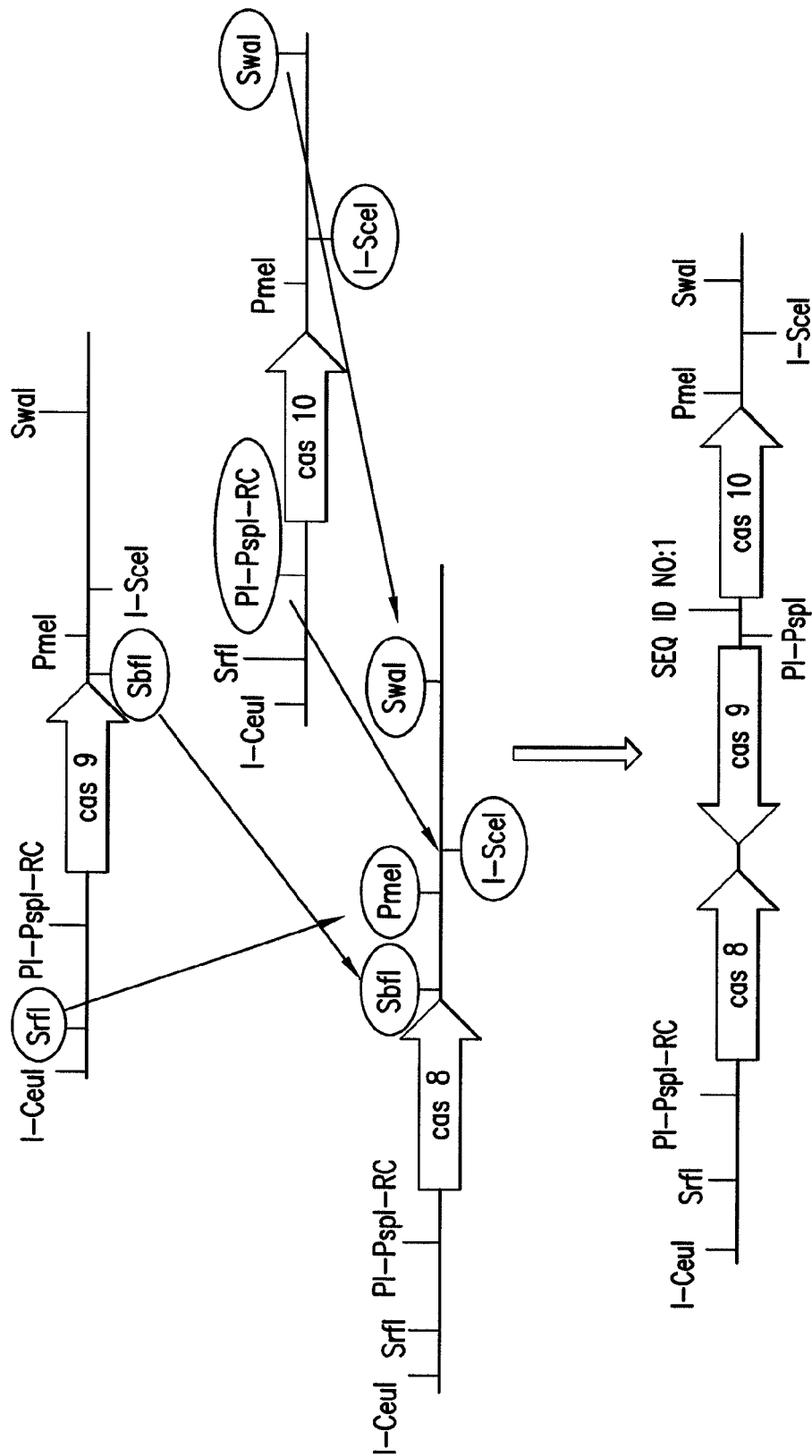
FIG. 12: Shows assembly of a double-stack vector in tail-to-tail orientation utilizing an additional overhang-generating restriction enzyme, SbfI. Subsequent addition of other cassettes is possible. The triple-cassette vector diagram only shows restriction sites that are available for further manipulations.

Construction of a Three-cassette Vector Stack in Tail-to-tail and Head-to-head Orientation By utilizing another overhang-generating restriction enzyme, SbfI, a cassette can be added in reverse orientation downstream of another cassette (FIG. 12). In first reactions, the vector containing cassette 8 is linearized by SbfI and PmeI digestion and cassette 9 is isolated by digestion with SrfI and SbfI. Combination of the purified linearized vector and cassette 9 fragment results in a double-stack vector with tail-to-tail orientation of cassettes 8 and 9. In subsequent reactions this double-stack vector is again linearized by I-SceI and SwaI digestion. Cassette 10 is isolated by PI-PspI and SwaI digestion and inserted into the linearized double-stack vector in head-to-head orientation to cassette 9 (See FIG. 12). Alternatively, the triple-stack vector can be generated by inserting an isolated cassette 10 fragment into a linearized vector containing cassette 8 and linearizing the resulting double-stack vector and inserting an isolated cassette 9. Because the fragment containing cassette 9 is inserted into the vector containing cassette 8 in reverse orientation the PI-PspI-RC site of fragment with cassette 9 is now located between cassettes 9 and 10 of the vector stack and because of the reverse orientation is now a PI-PspI site.

SrfI, PI-PspI-RC, PmeI, I-SceI, and SwaI are still available for further stacking purposes.

Example 7

Figure 13:
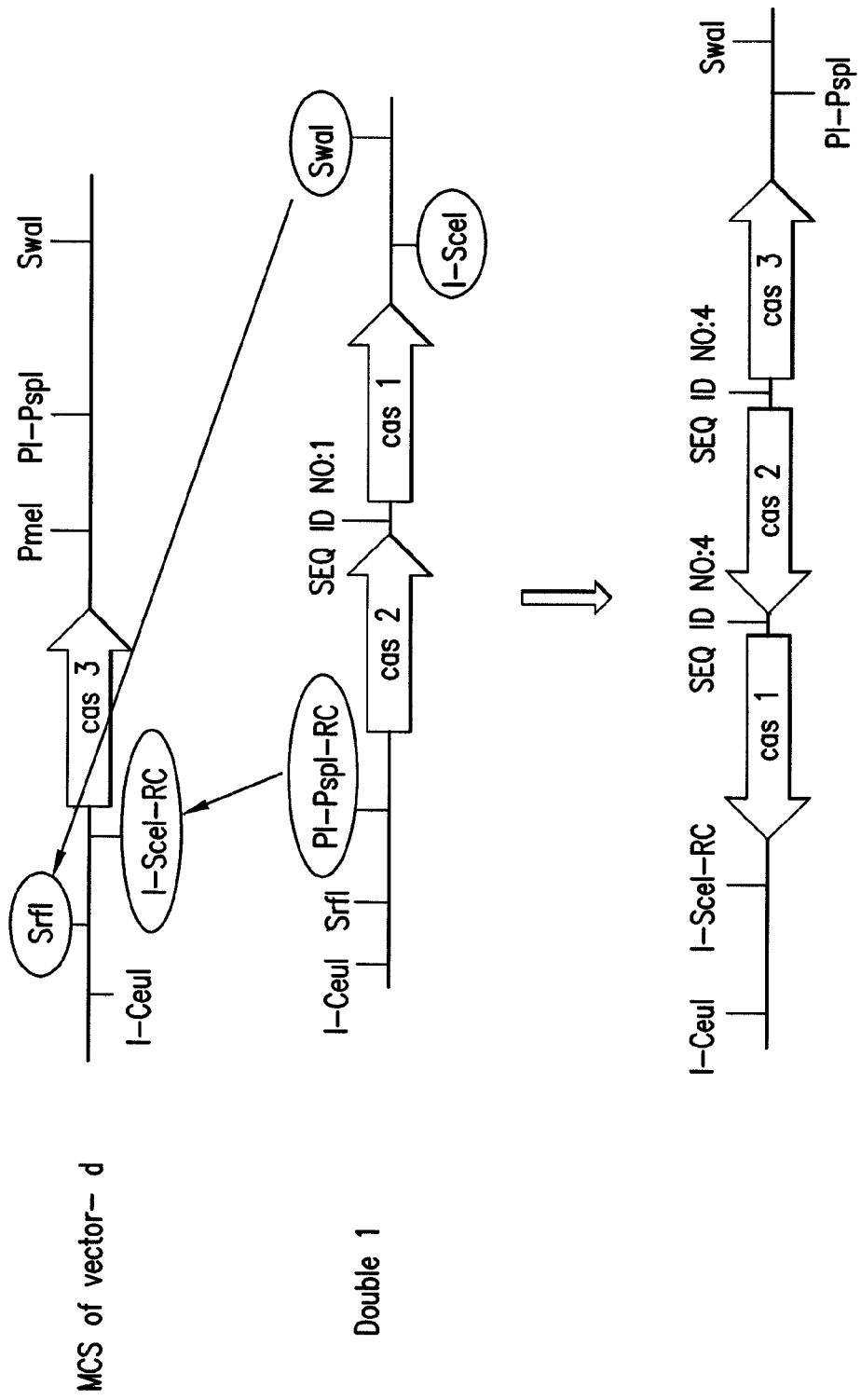
FIG. 13: Shows the construction of a triple-stack vector in head-to-tail, head-to-head orientation.

Construction of a Three-cassette Vector Stack with Head-to-tail and Head-to-head Orientation Using Vector Design MCS-d The vector stack Double 1, as created in Example 2, is isolated by digestion with PI-PspI and SwaI. To create a vector in head-to-tail, head-to-head configuration a vector containing cassette 3 in the configuration MCS-d (see FIG. 6) is used and is linearized by digestion with SrfI and I-SceI. Upon insertion, a triple-stack vector is generated with cassettes 1 and 2 in head-to-tail and cassettes 2 and 3 in head-to-head orientation (FIG. 13). Because the isolated fragment containing cassettes 2 and 1 is introduced into the vector with cassette 3 in reverse orientation, the recombined site between cassettes 1 and 2 now has the sequence of SEQ ID NO: 4 and the recombined site between cassettes 2 and 3 also has the sequence of SEQ ID NO: 4. Likewise, the I-SceI site from the fragment containing cassettes 1 and 2 has the reverse orientation of I-SceI-RC in the vector stack containing all three cassettes. I-CeuI, I-SceI-RC, PI-PspI and SwaI are available for further stacking manipulations.

Example 8

Figure 14:
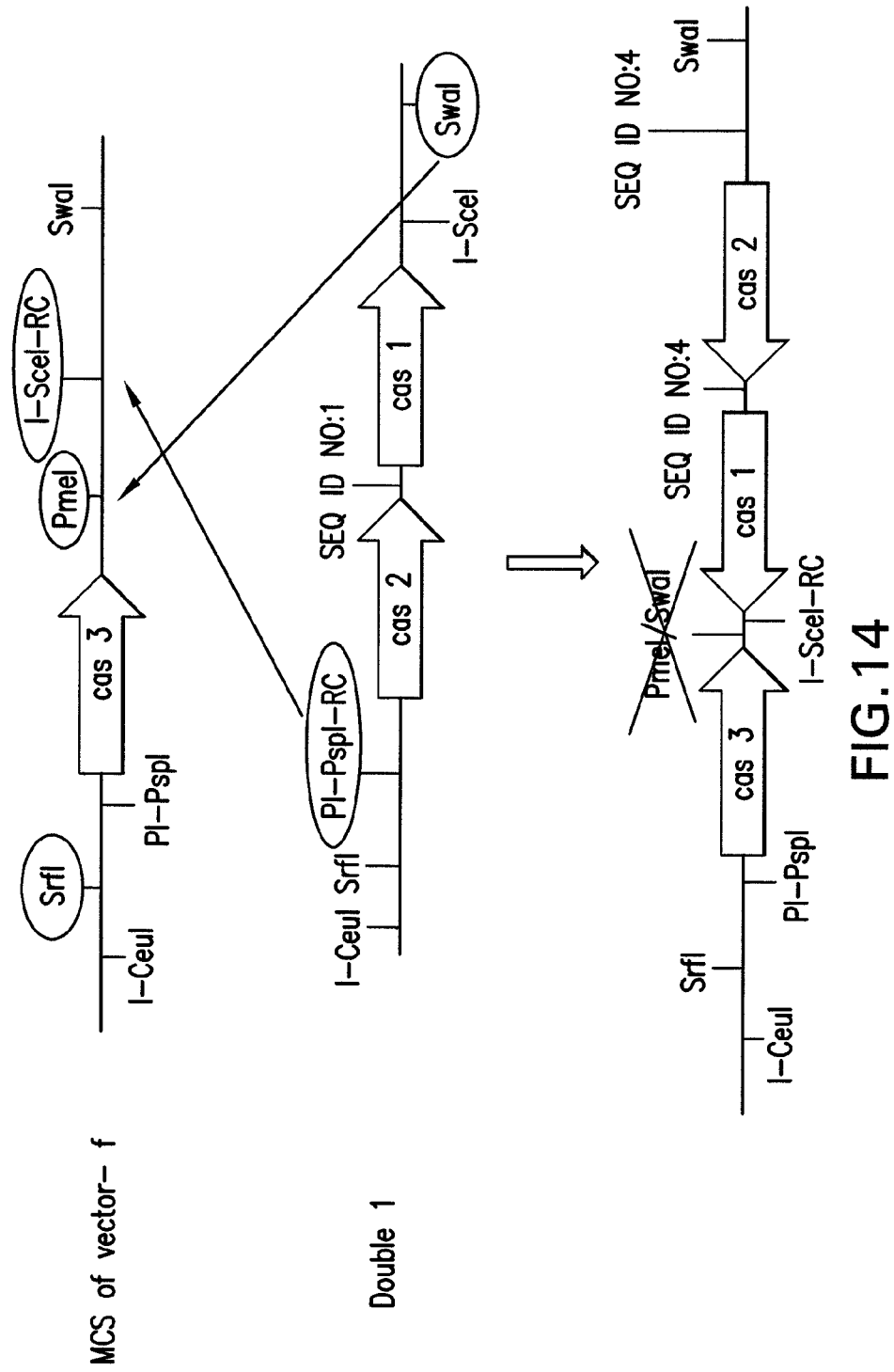
FIG. 14: Shows the construction of a triple-stack vector in tail-to-tail, head-to-tail orientation.

Construction of a Three Cassette Vector Stack with Tail-to-tail and Head-to-tail Orientation Using Vector Design MCS-f The vector stack Double 1, as created in Example 2, is isolated by digestion with PI-PspI and SwaI. To create a vector in tail-to-tail, head-to-tail configuration a vector containing cassette 3 in the configuration MCS-f (see FIG. 6) is used and is linearized by digestion with PmeI and I-SceI. Upon insertion, a triple-stack vector is generated with cassettes 3 and 1 in tail-to-tail and cassettes 1 and 2 in head-to-tail orientation (FIG. 14). Because the isolated fragment containing cassettes 2 and 1 is introduced into the vector with cassette 3 in reverse orientation, the recombined site between cassettes 1 and 2 now has the sequence of SEQ ID NO: 4 and the recombined site downstream of cassette 2 has the sequence of SEQ ID NO: 3. I-CeuI, SrfI, PI-PspI, and SwaI are available for further stacking manipulations and I-SceI-RC is located between cassettes 3 and 1.

Example 9

Figure 15:
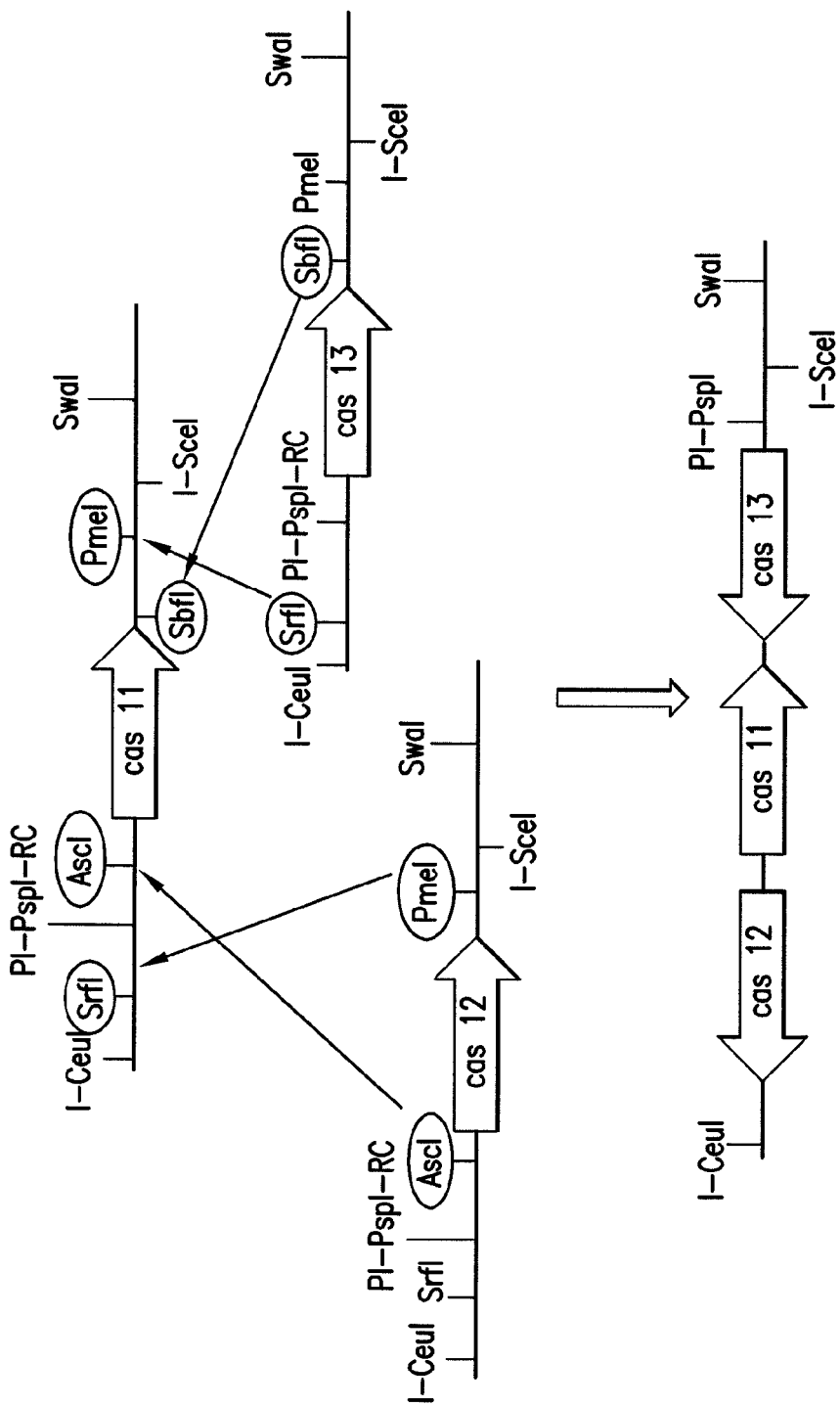
FIG. 15: Shows the construction of a triple-stack vector in head-to-head, tail-to-tail orientation. This triple-stack vector diagram can be used for further stacking (FIG. 16).

Construction of a Three Cassette Vector Stack with Head-to-head and Tail-to-tail Orientation The vector with cassette 11 is linearized by digestion with SrfI and AscI. Cassette 12 is isolated by digestion with AscI and PmeI and inserted into the linearized vector. In a subsequent reaction, the double-stack in head-to-head orientation of cassettes 12 and 11 is linearized with SbfI and PmeI digestion. Cassette 13 is isolated by digestion with SrfI and SbfI and inserted into the linearized double-stack vector. The resulting vector has I-CeuI, PI-PspI, I-SceI, and SwaI sites available for further manipulations (FIG. 15). Reversing the orientation of cassette 13 for insertion into the double-stack vector also reverses the orientation of the PI-PspI-RC site, which then becomes the regular PI-PspI restriction site.

Example 10

Construction of a Seven Cassette Vector Stack

Figure 16:
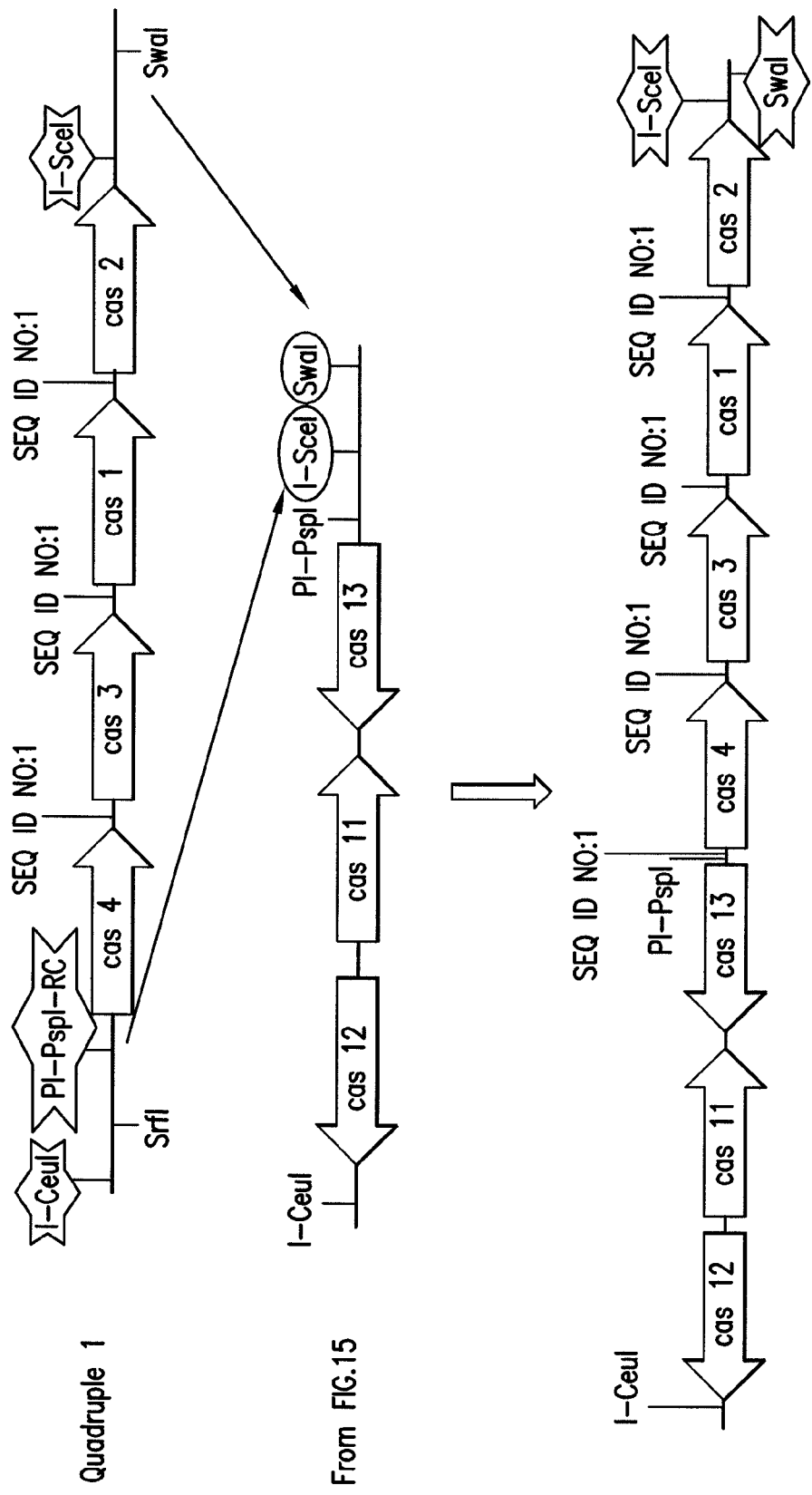
FIG. 16: Shows the construction of a seven-cassette vector. Generation of a four-cassette vector stack (Quadruple 1) is illustrated in FIG. 9.

The four-cassette vector stack generated in Example 4 (FIG. 9) is isolated by digestion with PI-PspI and SwaI, and the three-vector stack (FIG. 15 and Example 9) is linearized by digestion with I-SceI and SwaI. I-CeuI, I-SceI and SwaI are still available for further stacking in the resulting 7-cassette vector stack (FIG. 16).

Example 11

Construction of a Two-cassette Vector Stack Using Vector Design MCS-c

Figure 17:
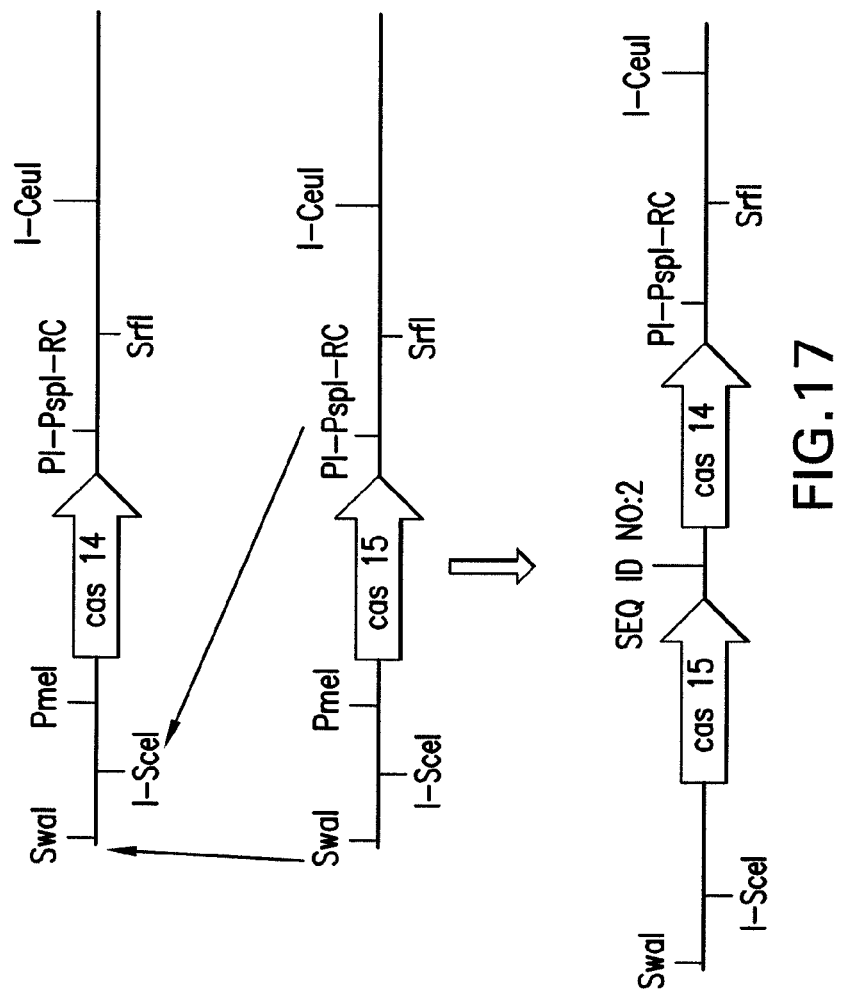
FIG. 17: Shows generation of SEQ ID NO:2 upon recombination using a vector diagram having an MCS configuration as shown in FIG. 6 (MCS of vector-c).

The same principles apply to generate vector stacks as described above. A two-vector stack can be generated by linearizing the vector with cassette 14 by SwaI and I-SceI digestion and isolating cassette 15 with SwaI and PI-PspI (FIG. 17). Upon recombination to build the double-stack vector, the recombined PI-PspI-RC/I-SceI site (SEQ ID NO:2) is no longer available for either PI-PspI or I-SceI digestion, but PI-PspI-RC and I-SceI sites are present in the double-vector stack due to the occurrence of PI-PspI-RC in the linearized vector and I-SceI in the isolated cassette 15 fragment.

Example 12

Construction of a Two-cassette Vector Stack Using Vector Designs MCS-c and MCS-e Linearizing the vector with cassette 16 by digestion with I-SceI and PmeI and isolating cassette 17 by digestion with PI-PspI and SwaI, followed by insertion of fragment with cassette 17 into the linearized vector results in a double stack vector in head-to-head orientation with SEQ ID NO:3 upstream of cassette 17 (FIG. 18).

What is claimed is:

1. A recombinant DNA molecule comprising the following restriction sites in order from 5' to 3':
   i) I-CeuI;
   ii) a restriction site that produces a blunt end;
   iii) PI-PspI or I-SceI;
   iv) a restriction site that produces a blunt end;
   v) I-SceI or PI-PspI but not the same as restriction site iii), and
   vi) a restriction site that produces a blunt end;
   wherein the overhangs produced by restriction site i) or iii) are capable of recombining with the overhang produced by restriction site v) such that recognition site i) or iii) is eliminated and restriction site v) is eliminated;
   wherein one of recognition sites iii) or v) is reverse complemented but not both; and
   wherein the restriction sites ii), iv) and vi) are different and selected from the group consisting of PmeI, SwaI, and SrfI.

2. The recombinant DNA molecule of claim 1, wherein restriction site iii) is I-SceI and restriction site v) is PI-PspI-RC.

3. The recombinant DNA molecule of claim 1, wherein restriction site iii) is I-SceI-RC and restriction site v) is PI-PspI.

4. The recombinant DNA molecule of claim 1, wherein digestion at restriction sites i) or iii) and v) produces the nucleic acid sequence of SEQ ID NO:1, 2, 3, or 4 upon recombination.

5. The recombinant DNA molecule of claim 1, further comprising at least one gene expression cassette between restriction sites iii) and iv).

6. The recombinant DNA molecule of any of claims 1-5, wherein said DNA molecule further comprises a vector.

7. A vector comprising the recombinant DNA molecule of claim 1.

8. The vector of claim 7, wherein restriction site iii) is in reverse complemented orientation.

9. The vector of claim 7, wherein restriction site v) is in reverse complemented orientation.

* * * * *